United States Patent [19]

Narula et al.

[11] Patent Number: 4,985,403

[45] Date of Patent: Jan. 15, 1991

[54] USE OF ADAMANTANE DERIVATIVES IN AUGMENTING OR ENHANCING THE AROMA OF CONSUMABLE MATERIALS

[75] Inventors: Anubhav P. S. Narula, Hazlet; Charles E. J. Beck, Summit; Marie R. Hanna, Keyport, all of N.J.

[73] Assignee: International Flavors & Fragrances Inc., New York, N.Y.

[21] Appl. No.: 545,623

[22] Filed: Jun. 29, 1990

Related U.S. Application Data

[63] Continuation-in-part of Ser. No. 261,275, Oct. 21, 1988, Pat. No. 4,956,481.

[51] Int. Cl.$^5$ .............................................. A61K 7/46
[52] U.S. Cl. ................................. 512/19; 252/174.11; 568/818; 560/256; 523/102
[58] Field of Search .................... 512/19; 568/818; 560/256

[56] References Cited

U.S. PATENT DOCUMENTS

| | | | |
|---|---|---|---|
| 3,996,169 | 12/1976 | Light et al. ...................... | 252/522 |
| 4,036,892 | 7/1977 | Inamoto et al. ................. | 260/617 F |
| 4,036,893 | 7/1977 | Inamoto et al. ................. | 260/617 F |
| 4,169,958 | 10/1979 | Inamoto et al. ................. | 568/668 |
| 4,439,354 | 3/1984 | Light et al. ...................... | 252/522 R |

FOREIGN PATENT DOCUMENTS 2054557  2/1981  United Kingdom ................. 512/19

OTHER PUBLICATIONS

Mlinaric-Majerski and Majerski, J. Am. Chem. Soc. 1983, pp. 7389–7395.

Hallden-Abberton, J. Org. Chem., vol. 46, 3, 1981, pp. 538–546.

Drivas and Mison, Tetrahedron Letters, vol. 22, 1981, pp. 641–644, "Nouvelle Methode de Synthese du Dimethyl-1,3 Adamantanol-2 et du Dimethyl-1,5 Adamantanol-2 Syn".

Primary Examiner—James H. Reamer
Attorney, Agent, or Firm—Arthur L. Liberman

[57] ABSTRACT

Described are adamantane derivatives defined according to the structure:

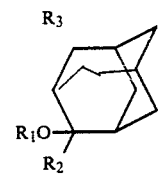

wherein $R_1$ is hydrogen or acetyl; $R_2$ is hydrogen or methyl; and $R_3$ is hydrogen or methylene ($CH_2$) and wherein the dashed line represents a carbon-hydrogen single bond or a carbon-methylene double bond with the provisos that when $R_2$ is methyl $R_1$ and $R_3$ are both hydrogen and when $R_2$ is hydrogen, $R_3$ is methylene and the dashed line is a carbon-methylene double bond and uses thereof in augmenting or enhancing the aroma of consumable materials selected from the group consisting of perfume compositions, colognes and perfumed articles.

7 Claims, 17 Drawing Sheets

GLC PROFILE FOR EXAMPLE I.

FIG. 2 NMR SPECTRUM FOR EXAMPLE I.

GLC PROFILE FOR EXAMPLE II.

GLC PROFILE FOR EXAMPLE III.

GLC PROFILE FOR EXAMPLE IV.

FIG. 8 NMR SPECTRUM FOR EXAMPLE IV, PEAK "70" OF FIG. 7.

N.M.R. SPECTRUM FOR EXAMPLE IV, PEAK "73" OF FIG. 7.

GLC PROFILE FOR EXAMPLE V.

IR SPECTRUM FOR EXAMPLE V.

GLC PROFILE FOR EXAMPLE VI.

IR SPECTRUM FOR EXAMPLE VI, PEAK "140" OF FIG.14.

USE OF ADAMANTANE DERIVATIVES IN AUGMENTING OR ENHANCING THE AROMA OF CONSUMABLE MATERIALS

BACKGROUND OF THE INVENTION

The present invention relates to adamantane derivatives defined according to the generic structure:

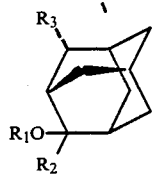

wherein $R_1$ is hydrogen or acetyl; $R_2$ is hydrogen or methyl; and $R_3$ is hydrogen or methylene and the dashed line represents a carbon-hydrogen single bond or a carbon-methylene double bond with the provisos that when $R_2$ is methyl, $R_1$ and $R_3$ are hydrogen and when $R_2$ is hydrogen, $R_3$ is methylene and the dashed line represents a carbon-methylene double bond and uses of such compounds in augmenting or enhancing the aroma of perfume compositions, perfumed articles and colognes.

There has been considerable work performed relating to substances which can be used to impart (modify, augment or enhance) fragrances too (or in) various consumable materials. Such substances are used to diminsh the use of expensive natural materials some of which may be in short supply and to provide more uniform properties in the finished product.

Woody, earthy, camphoraceous, phenolic, piney, balsamic and patchouli aromas with camphoraceous, armoise, animalic, woody and minty topnotes are particularly desirable in several types of perfume compositions, perfumed articles and colognes.

The use of tricyclic alcohol derivatives in perfumery for augmenting or enhancing the aromas of perfume compositions, perfumed articles and colognes is well known in the art. Thus, Inamoto, et al in U.S. Pat. No. 4,036,893 discloses the use in perfumery of the compound having the structure:

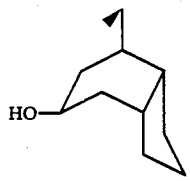

Inamoto, et al in U.S. Pat. No. 4,169,958 also discloses the use of the tricyclic alcohol having the structure:

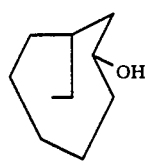

in perfumery. Light, et al in U.S. Pat. No. 3,996,169 discloses the use of the compound having the structure:

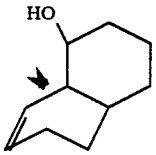

in perfumery. Inamoto, et al in U.S. Pat. No. 4,169,958 also discloses the use of the tricyclic alcohol having the structure:

in perfumery. Light, et al in U.S. Pat. No. 3,996,169 discloses the use of the compound having the structure:

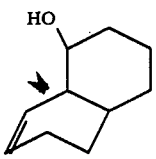

in perfumery. Inamoto, et al in U.S. Pat. No. 4,036,892 discloses the use of the compound having the structure:

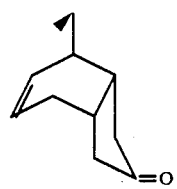

and in U.S. Pat. No. 4,036,892 discloses the use in perfumery of the compound having the structure:

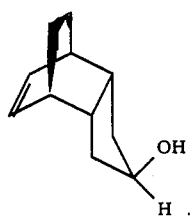

The use in perfumery of the compound having the structure:

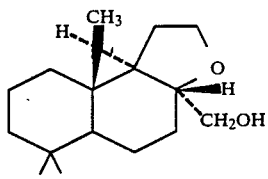

is disclosed in Chemical Abstracts, Volume 109, 9, 1988, No. 6759v (abstract of Koltsa, et al, Zh.Obshch.Khim., 1987, 57 (11) 2620-9.

Light, et al in U.S. Pat. No. 4,439,354 discloses the genus of compounds defined according to the structure:

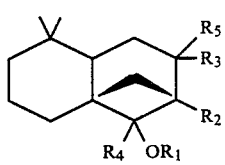

for use in perfumery wherein $R_1$ represents hydrogen, methyl or acetyl and $R_2$, $R_3$, $R_4$ and $R_5$ each represent hydrogen, methyl or ethyl.

Light, et al in U.S. Pat. No. 3,996,169 discloses the genus of compounds defined according to the structure:

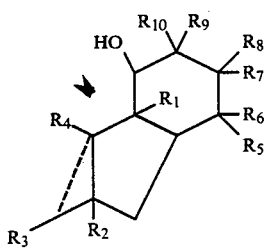

where one or more of the R groups represents hydrogen or methyl.

Adamantane derivatives and adamantane itself are known for use in augmenting or enhancing the aroma of perfume compositions, perfumed articles and colognes. Thus, the perfume use of compounds having the structures:

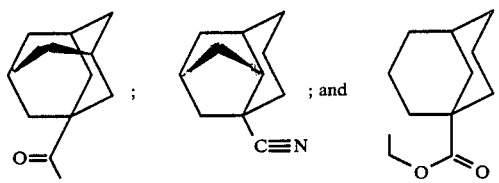

is disclosed in Chemical Abstracts, Volume 71, No. 94695w (abstract of Netherlands Published Application No. 6715903, May 28, 1969). Japan Kokai 75/25742 Published on Mar. 18, 1975 and abstracted at Chem.Abstracts, Volume 84, No. 35214j and Japan Kokai Tokkyo Koho 78/145920 Published on Dec. 19, 1978 and abstracted at Chem.Abstracts, Volume 90, No. 142085p discloses the perfume use of adamantane itself having the structure:

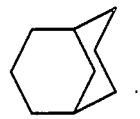

Synthesis of various oxygen-substituted adamantane derivatives is well known in the prior art.

Mlinaric-Magerski and Magerski, J.Am.Soc., 1983, 105, pages 7389-7395 discloses the compound having the structure:

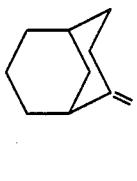

at page 7390 and discloses the reaction sequence:

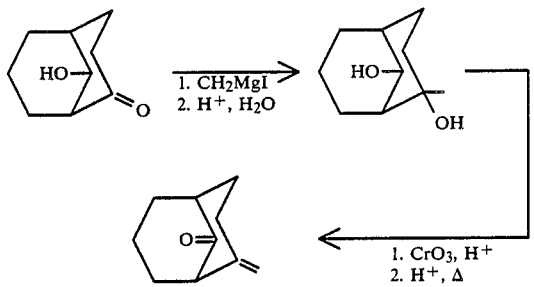

at page 7389.

Hallden-Aberton, J.Org.Chem., Volume 46, No. 3, 1981, pages 538-546 discloses the reaction sequence:

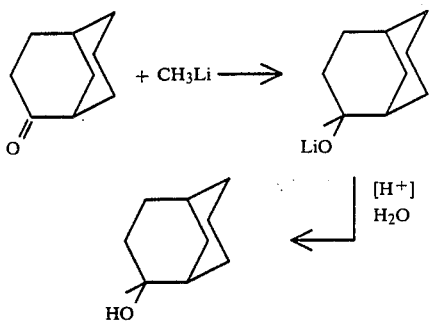

at pages 539 and 544.

Drivas & Mison, Tetrahedron Letters, Volume 22, 1981, at pages 641-644 discloses at page 643 the reaction sequence:

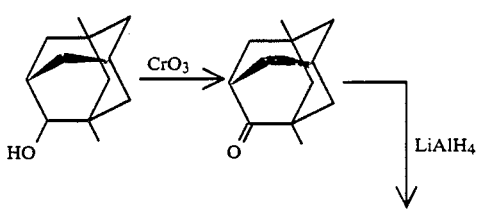

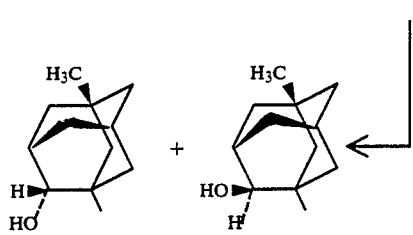

Kovalev, et al, Chem.Abstracts, Volume 109, 1988, No. 22553d (abstract of Zh.Org.Khim., 1987, 23(9), 1882–6 disclosed the compounds having the structure:

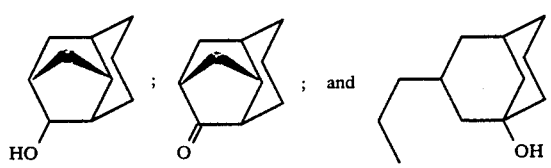

and discloses the reaction sequence:

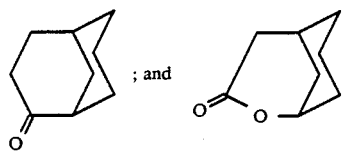

However, the adamantane derivatives of our invention have unexpected, unobvious and advantageous properties with respect to the compounds of the prior art. Nothing in the prior art explicitly or implicitly sets forth the adamantane derivatives of our invention or their uses.

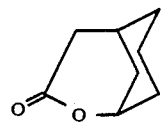

(conditions: SE-30 column programmed at 220° C. isothermal).

Figure 2:
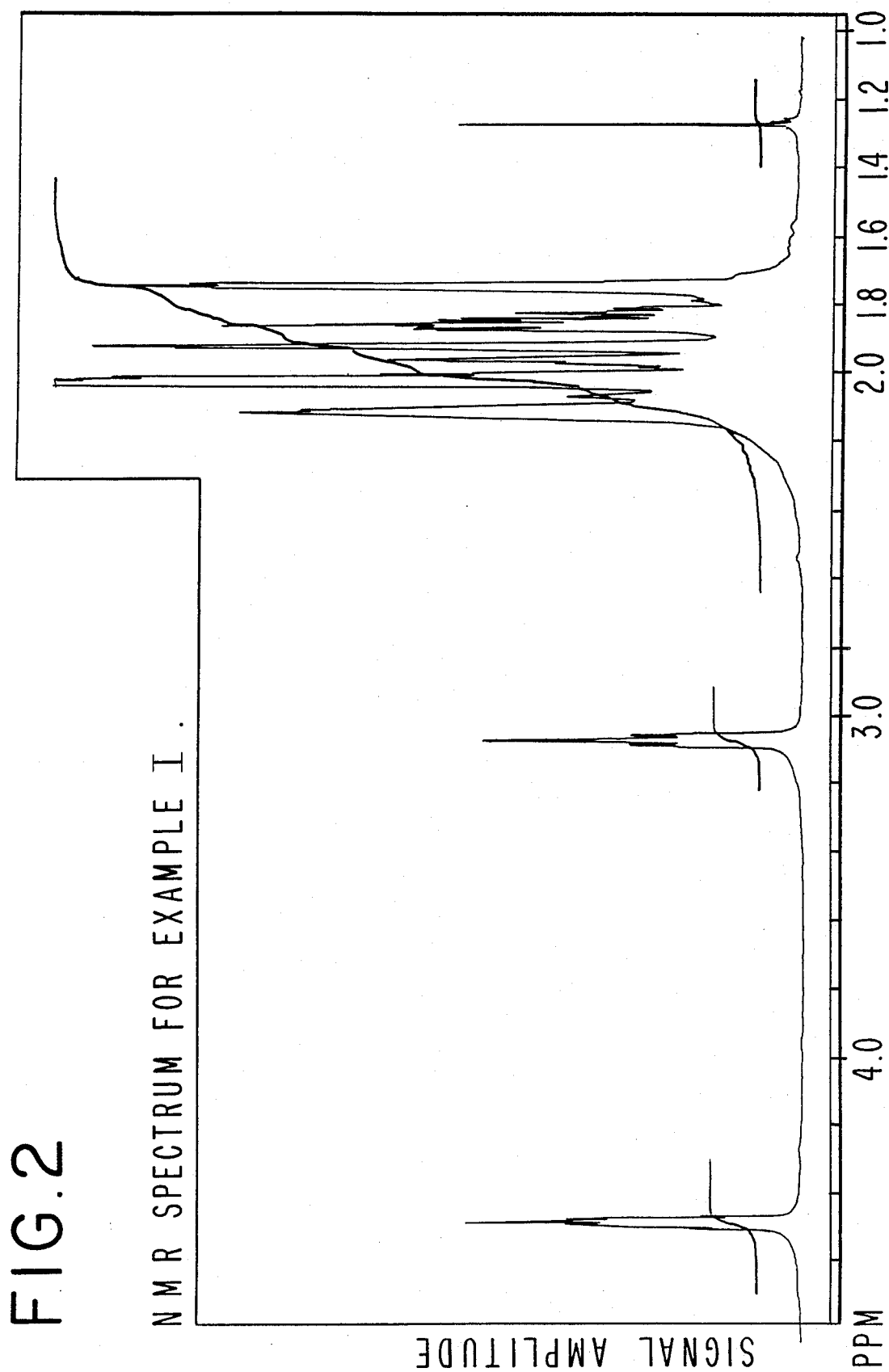

FIG. 2 is the NMR spectrum for the compound having the structure:

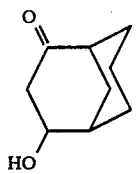

produced according to Example I.

Figure 3:
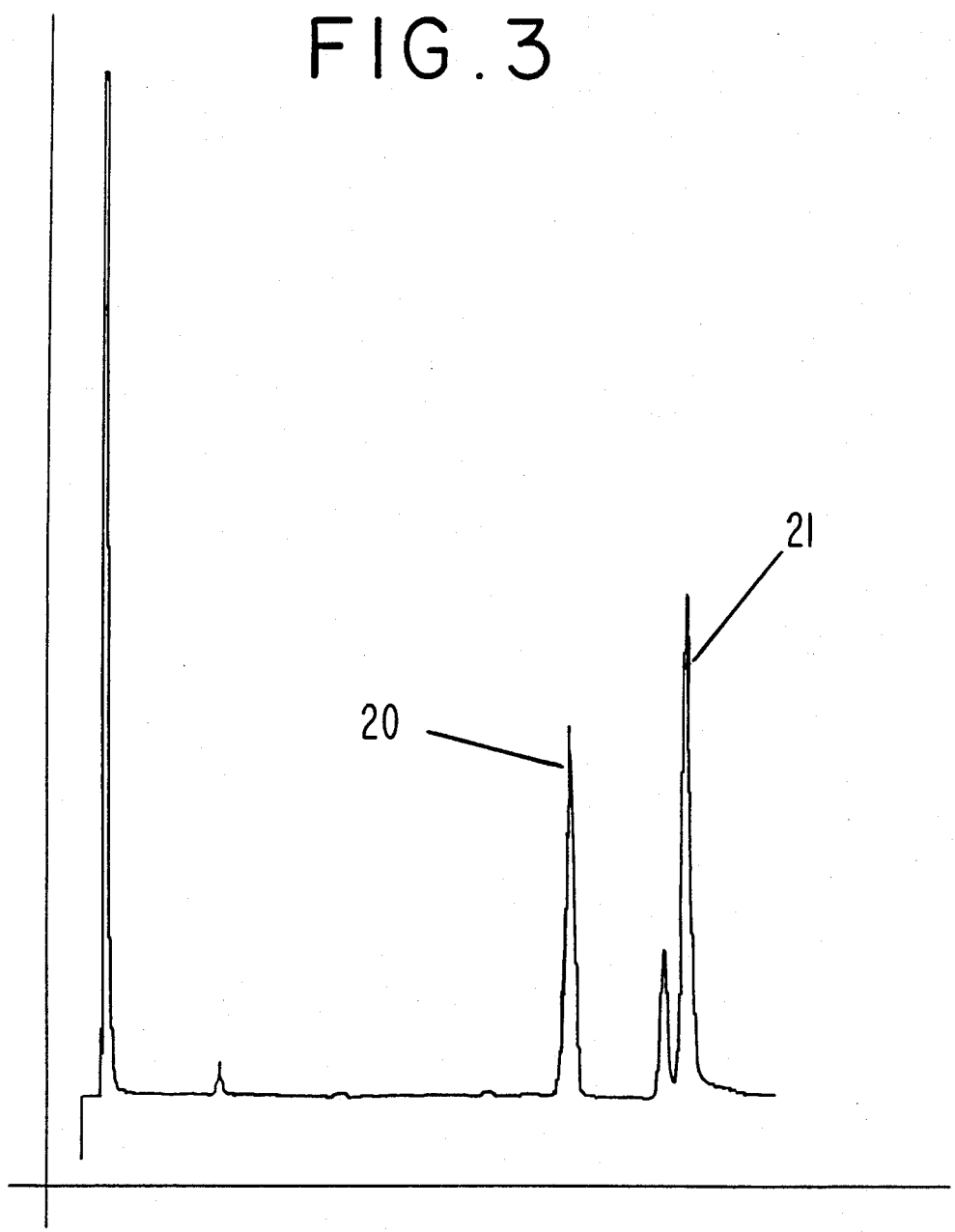

FIG. 3 is the GLC profile for the crude reaction product of Example II containing the compounds having the structures:

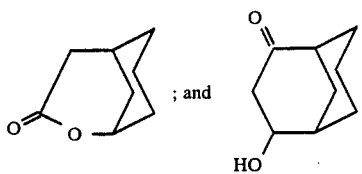

Figure 4:
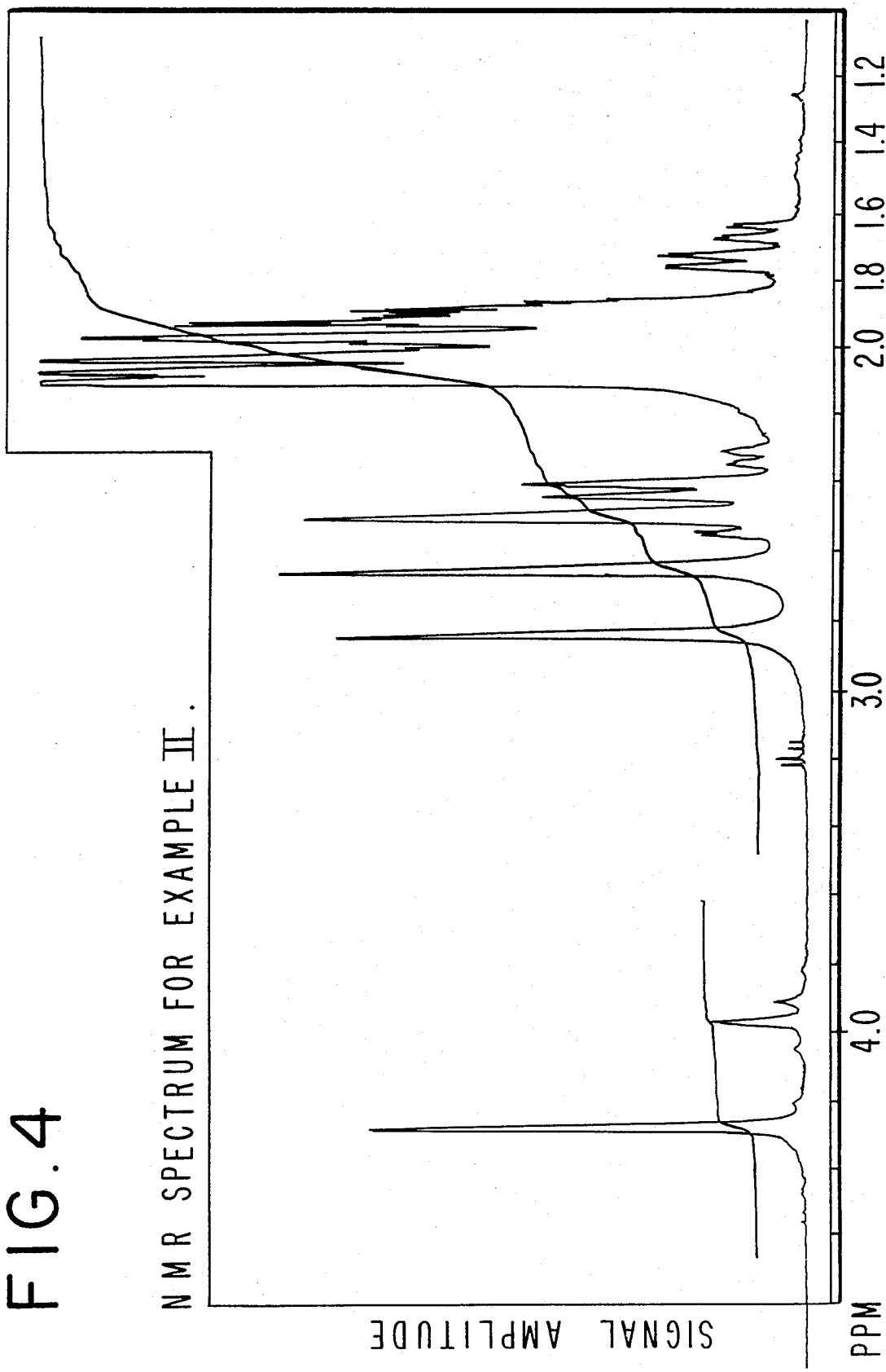

FIG. 4 is the NMR spectrum for compound having the structure:

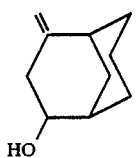

prepared according to Example II.

Figure 5:
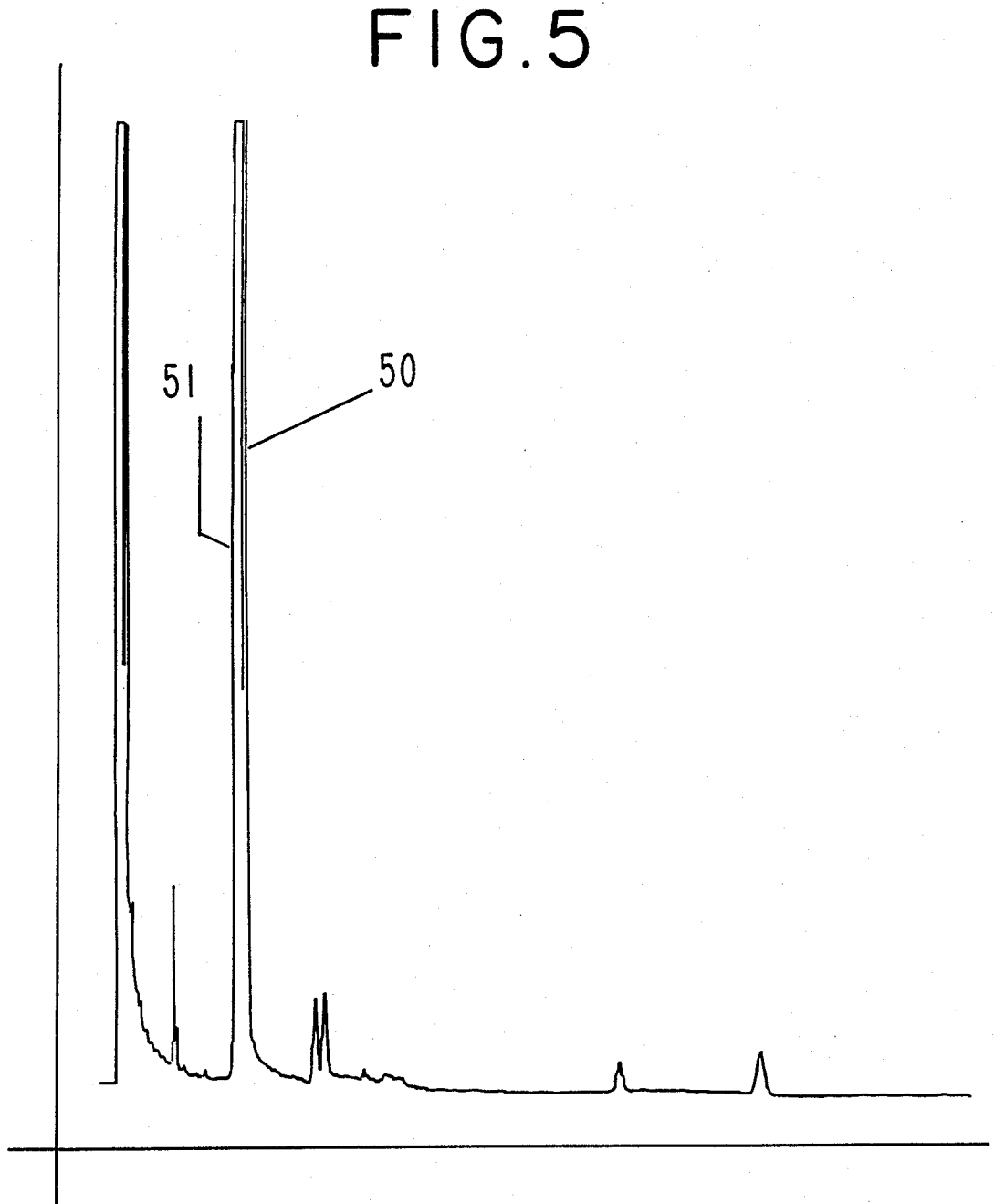

FIG. 5 is the GLC profile for the reaction product of Example III containing the compound having the structure:

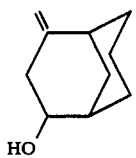

Figure 6:
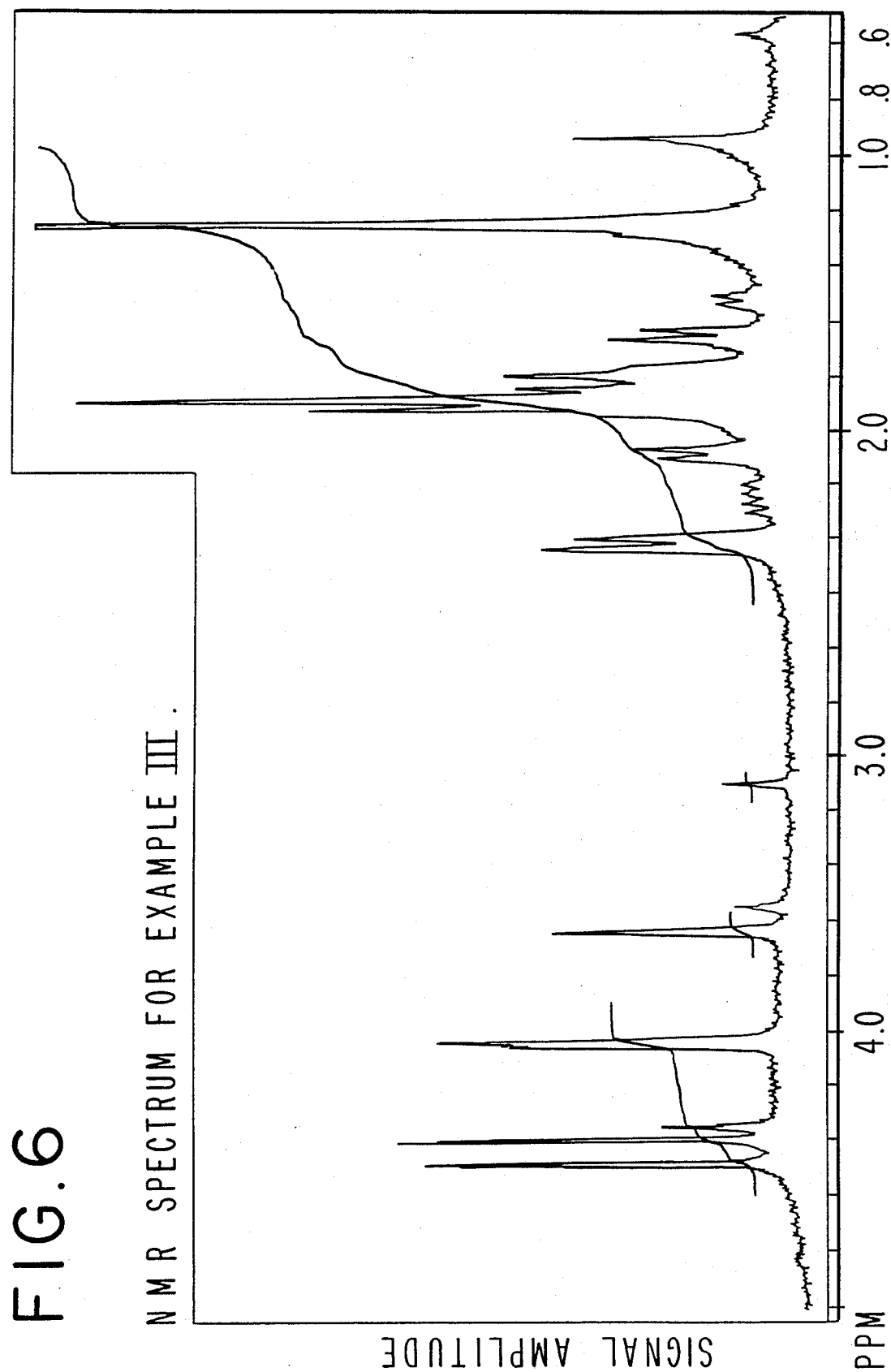

FIG. 6 is the NMR spectrum for the compound having the structure:

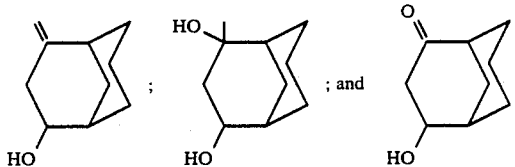

prepared according to Example III.

Figure 7:
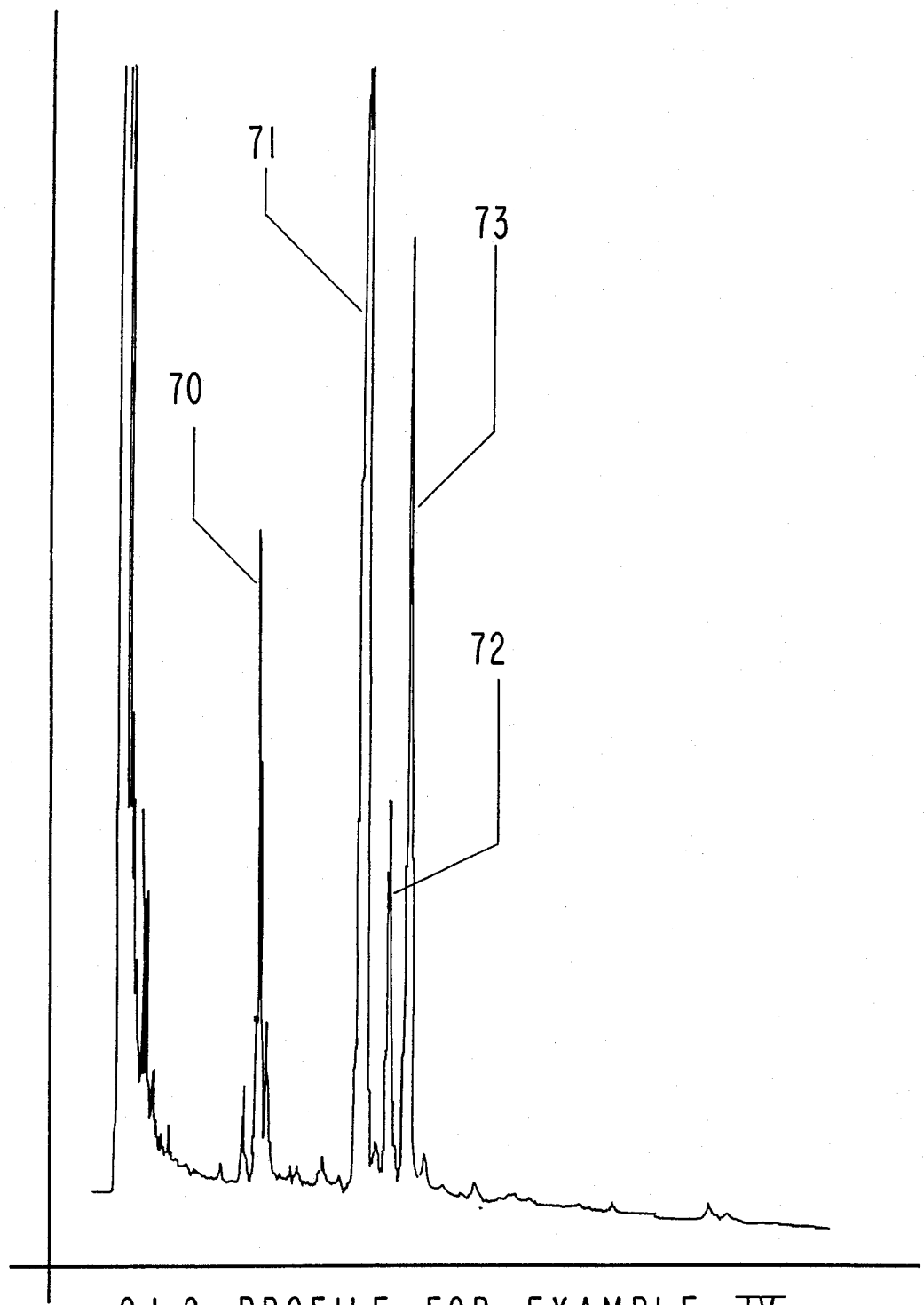
Figure 8:
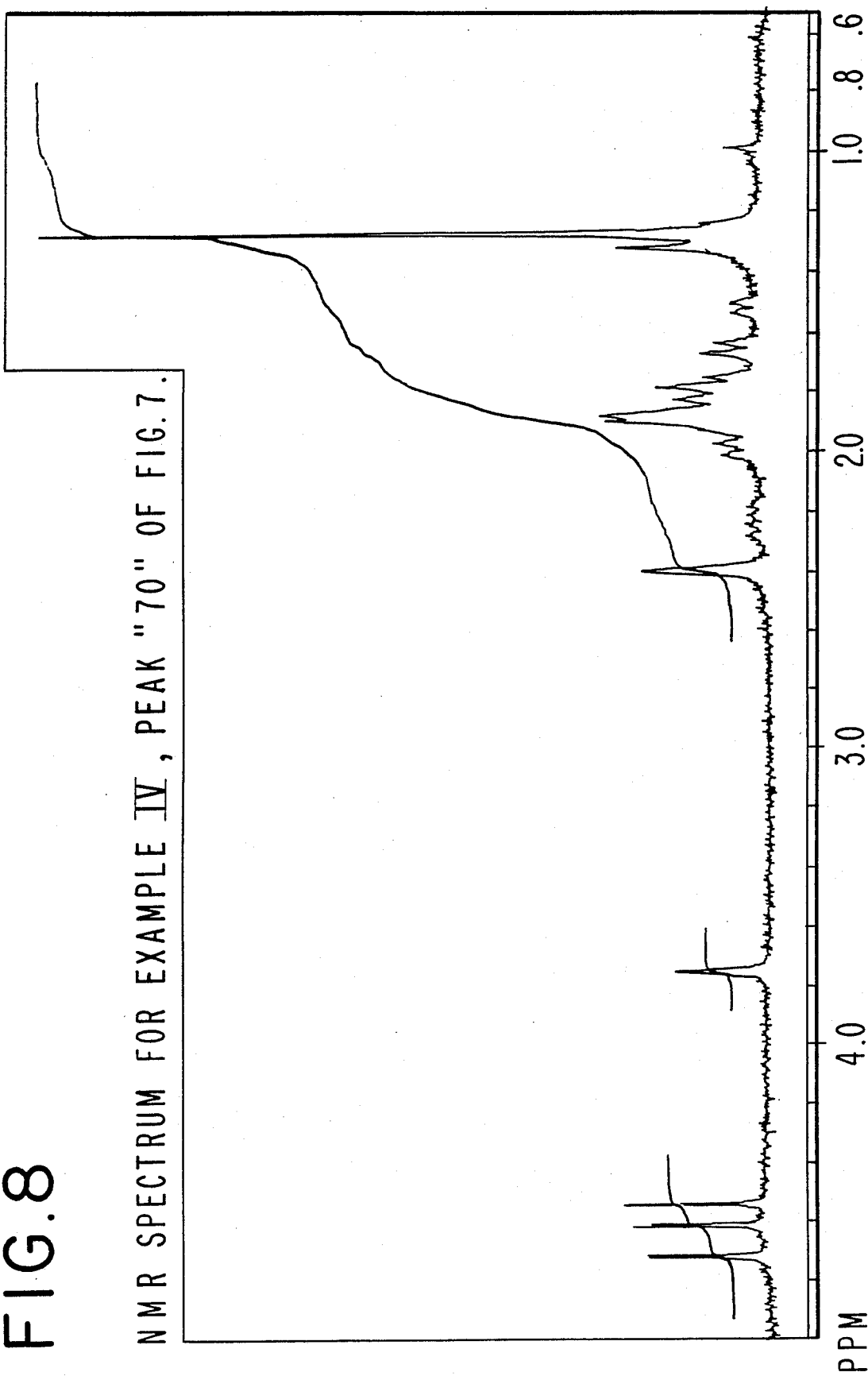

FIG. 7 is the GLC profile for the crude reaction product of Example IV and sets forth and peaks for the compounds having the structures:

FIG. 8 is the NMR spectrum for the peak indicated by reference numeral 70 of FIG. 7 for the compound having the structure:

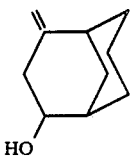

Figure 9:
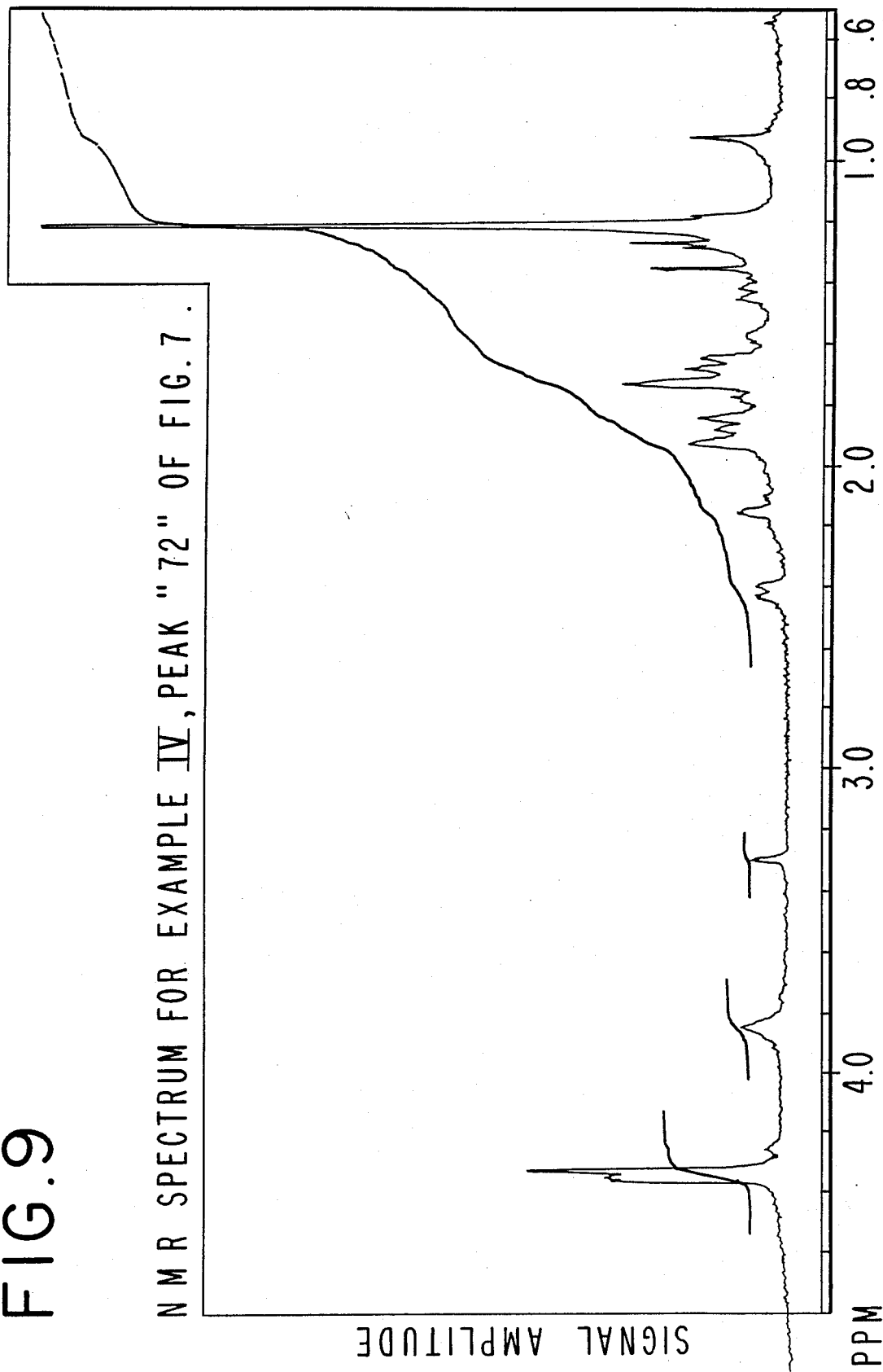

FIG. 9 is the NMR spectrum for the peak indicated by reference numeral 72 of FIG. 7 for the compound having the structure:

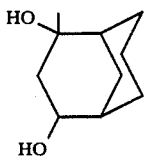

Figure 10:
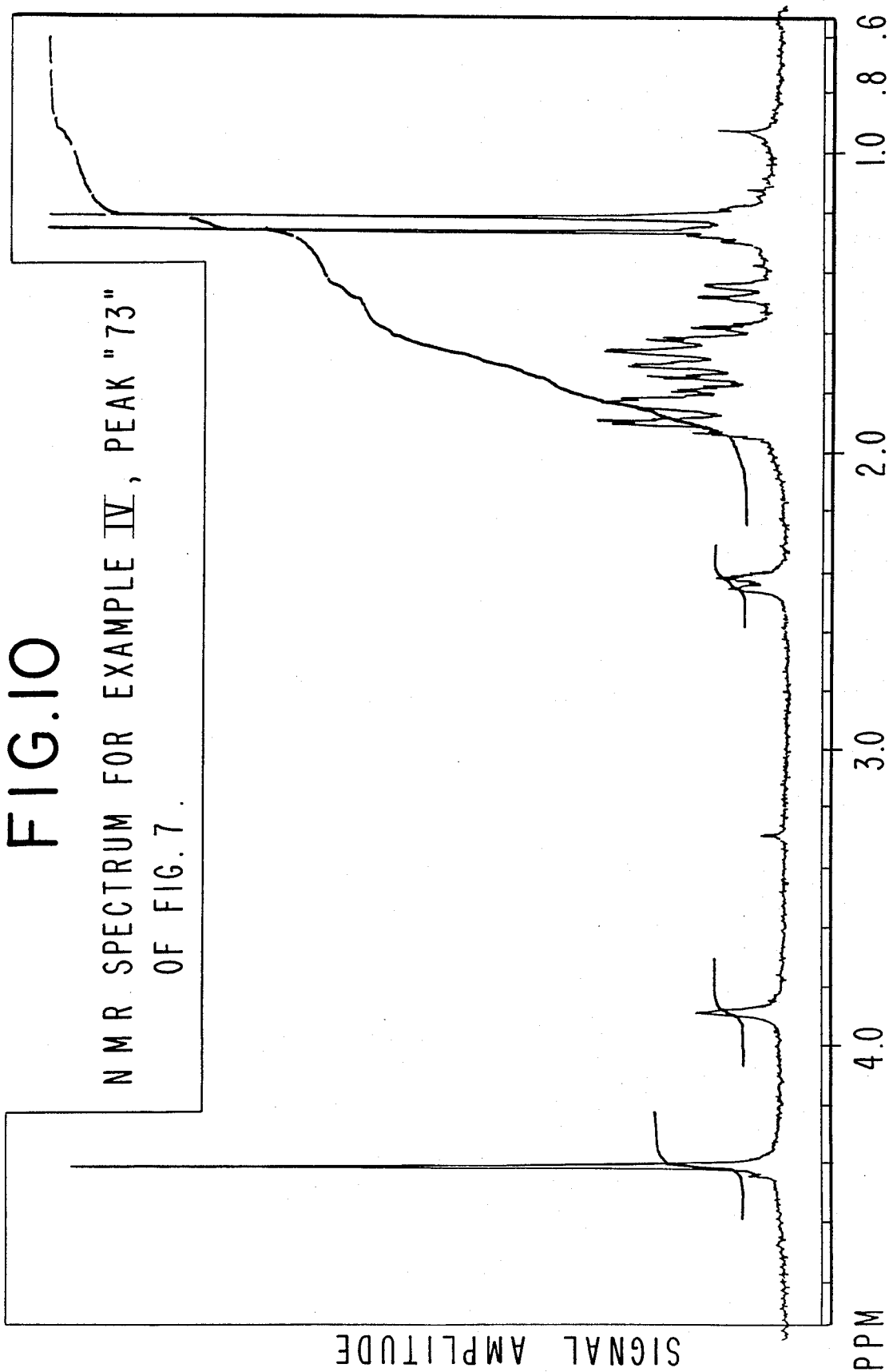

FIG. 10 is the NMR spectrum for the peak indicated by reference numeral 73 of FIG. 7 for the compound having the structure:

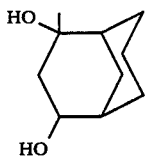

Figure 11:
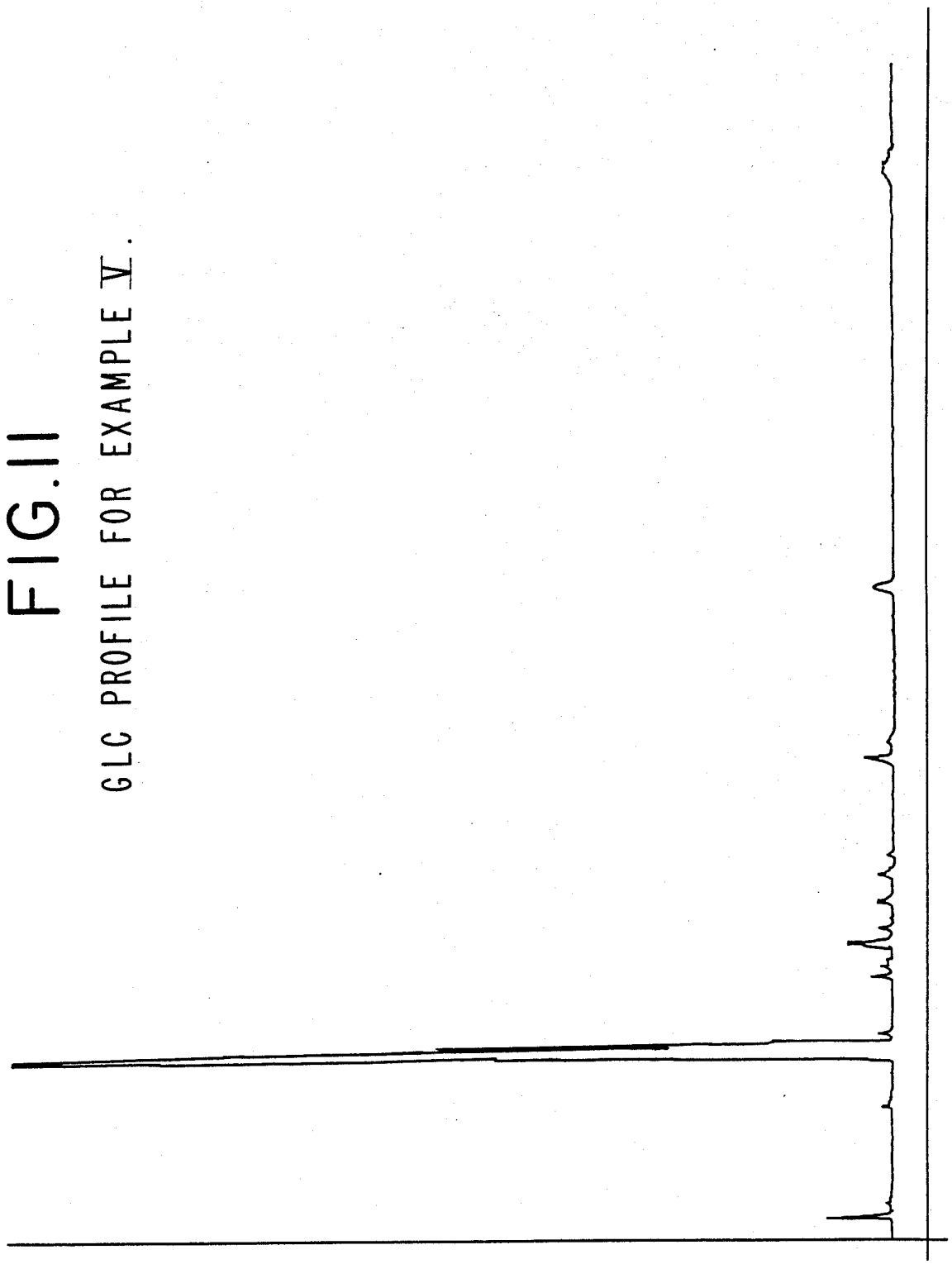

FIG. 11 is the GLC profile for the reaction product of Example V containing the compound having the structure:

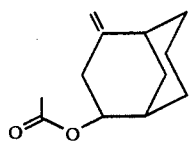

Figure 12:
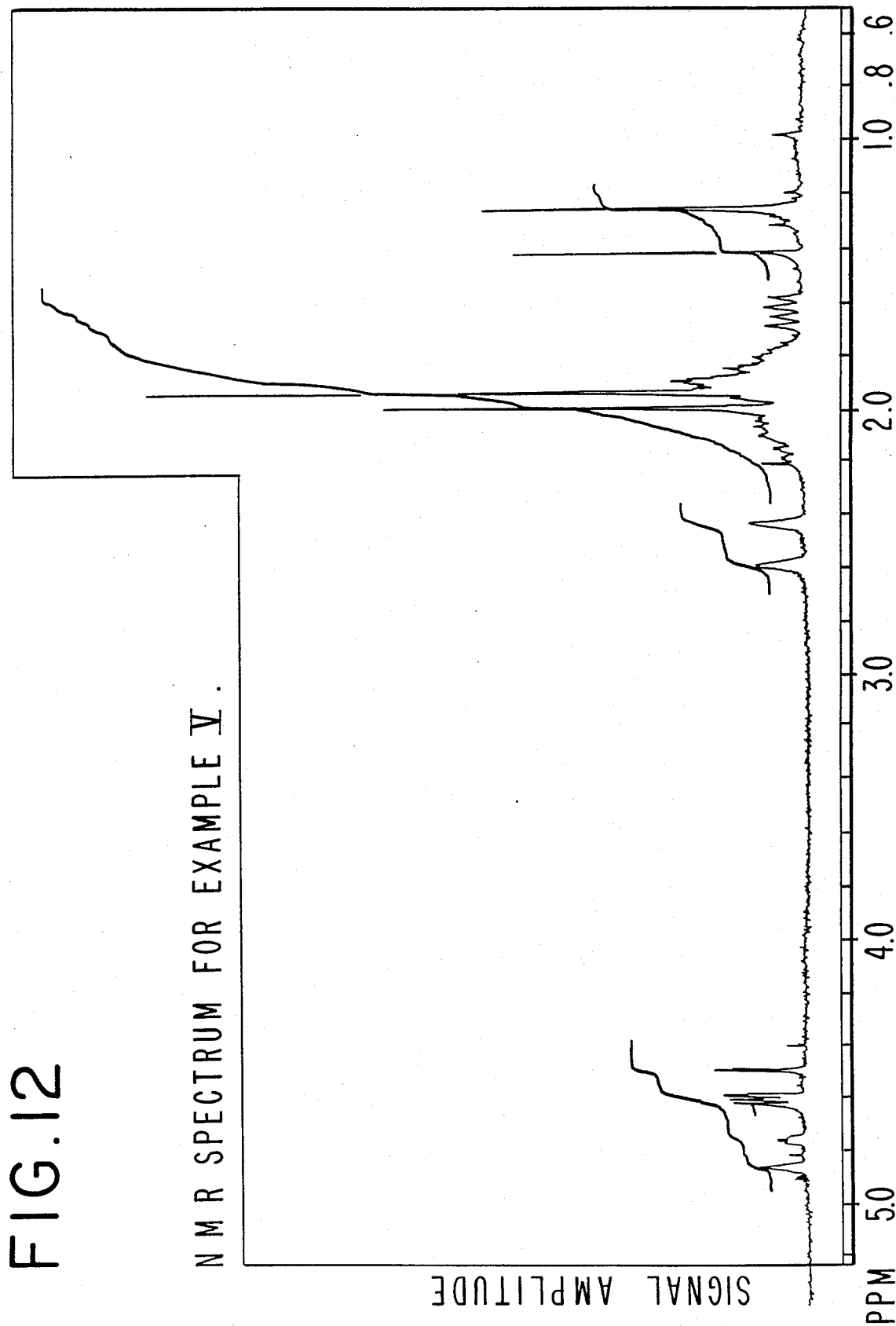
Figure 13:
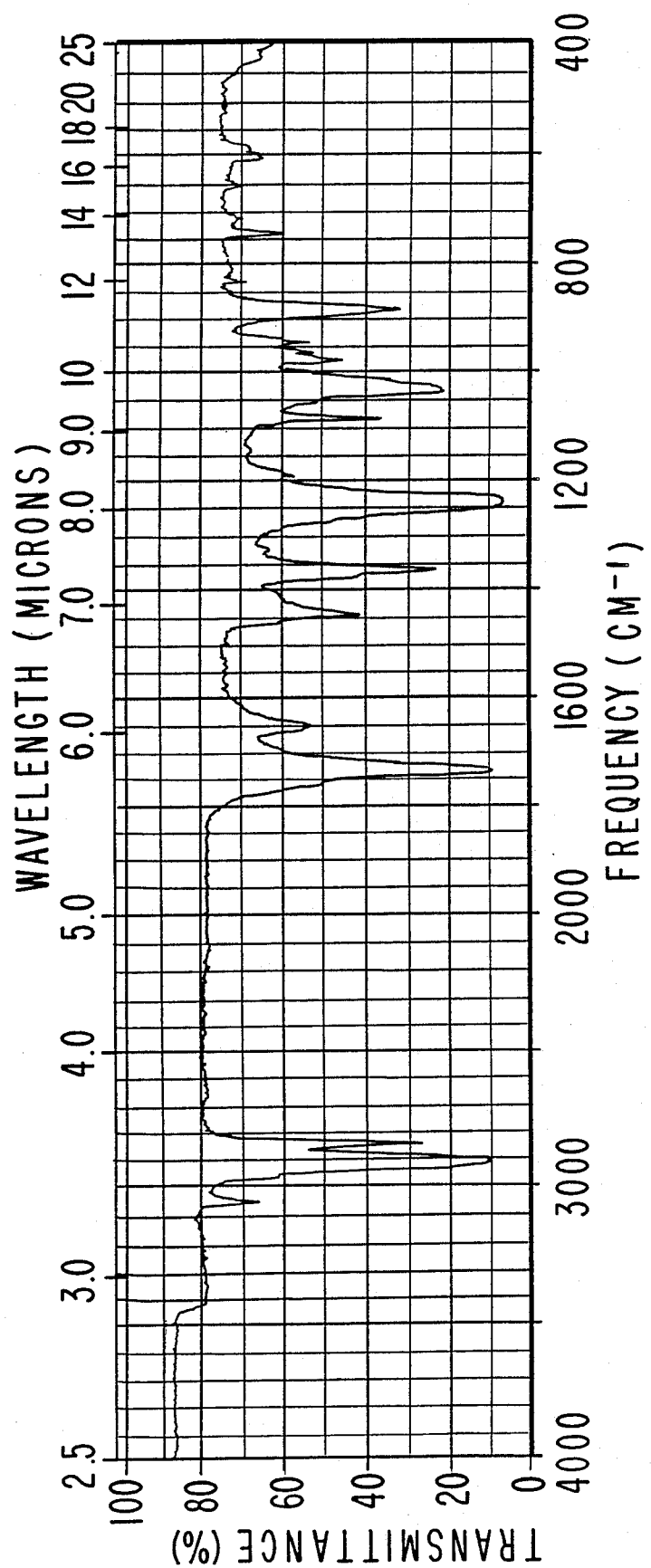

FIG. 12 is the NMR spectrum for the compound having a the structure:

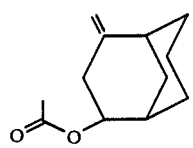

prepared according to Example V.
FIG. 13 is the infra-red spectrum for the compound having the structure:

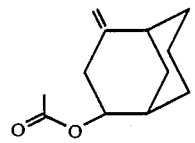

prepared according to Example V.

Figure 14:
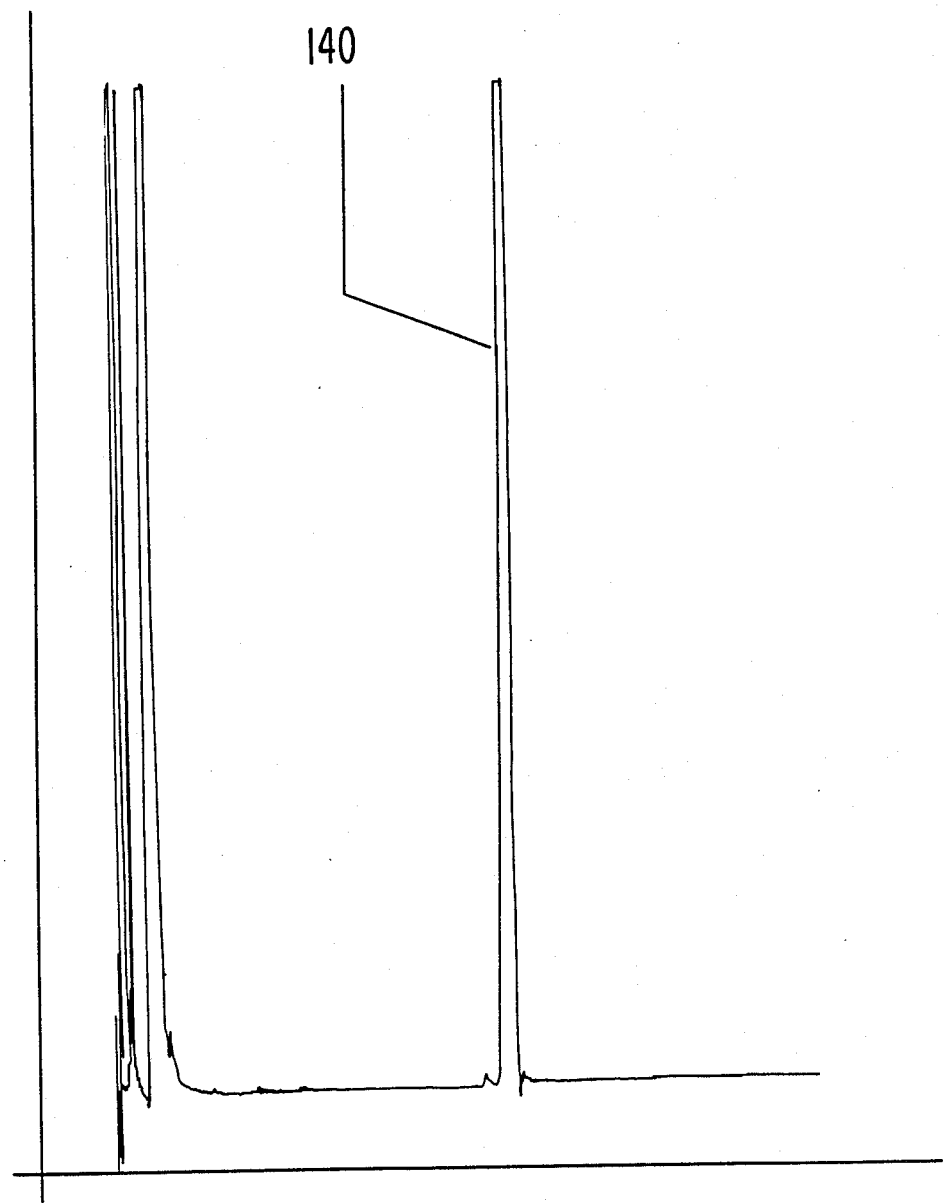

FIG. 14 is the GLC profile for the crude reaction product of Example VI containing the compound having the structure:

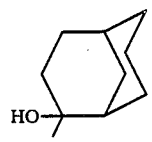

(Conditions: Carbowax column programmed at 100°–200° C. at 8° C. per minute).

Figure 15:
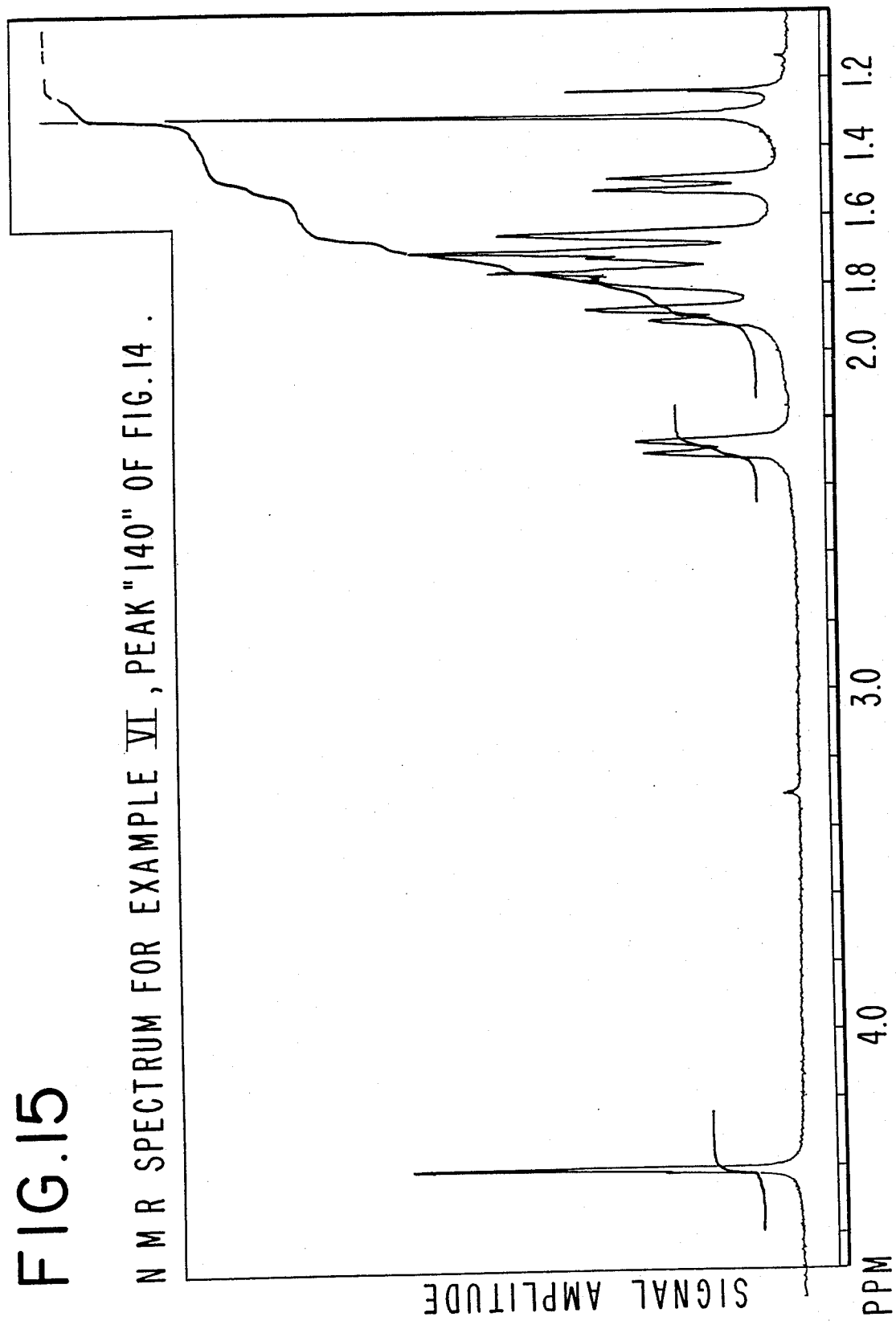

FIG. 15 is the NMR spectrum for the peak indicated by reference numeral 140 of FIG. 14 for the compound having the structure:

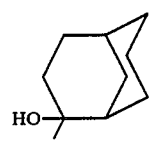

Figure 16:
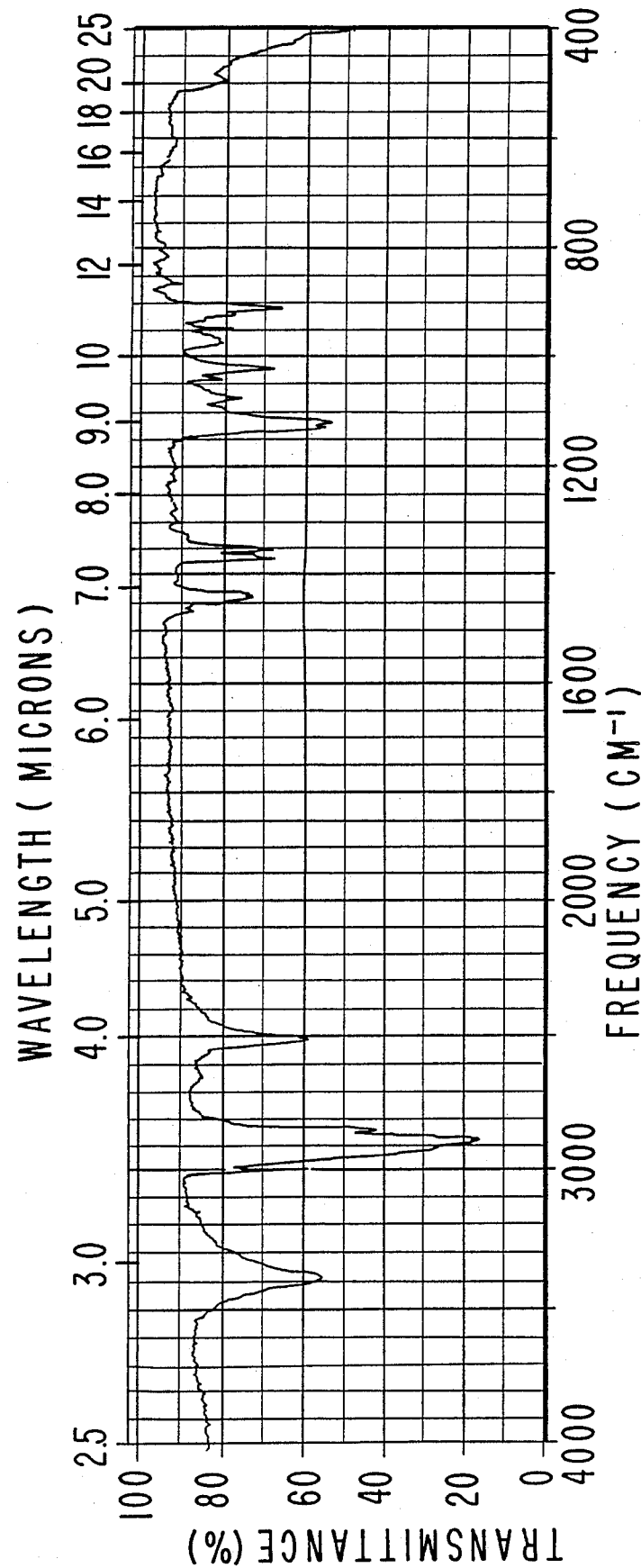

FIG. 16 is the infra-red spectrum for the peak indicated by reference numeral 140 of the GLC profile of FIG. 14 for the compound having the structure:

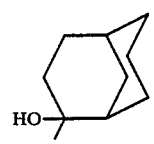

Figure 17:
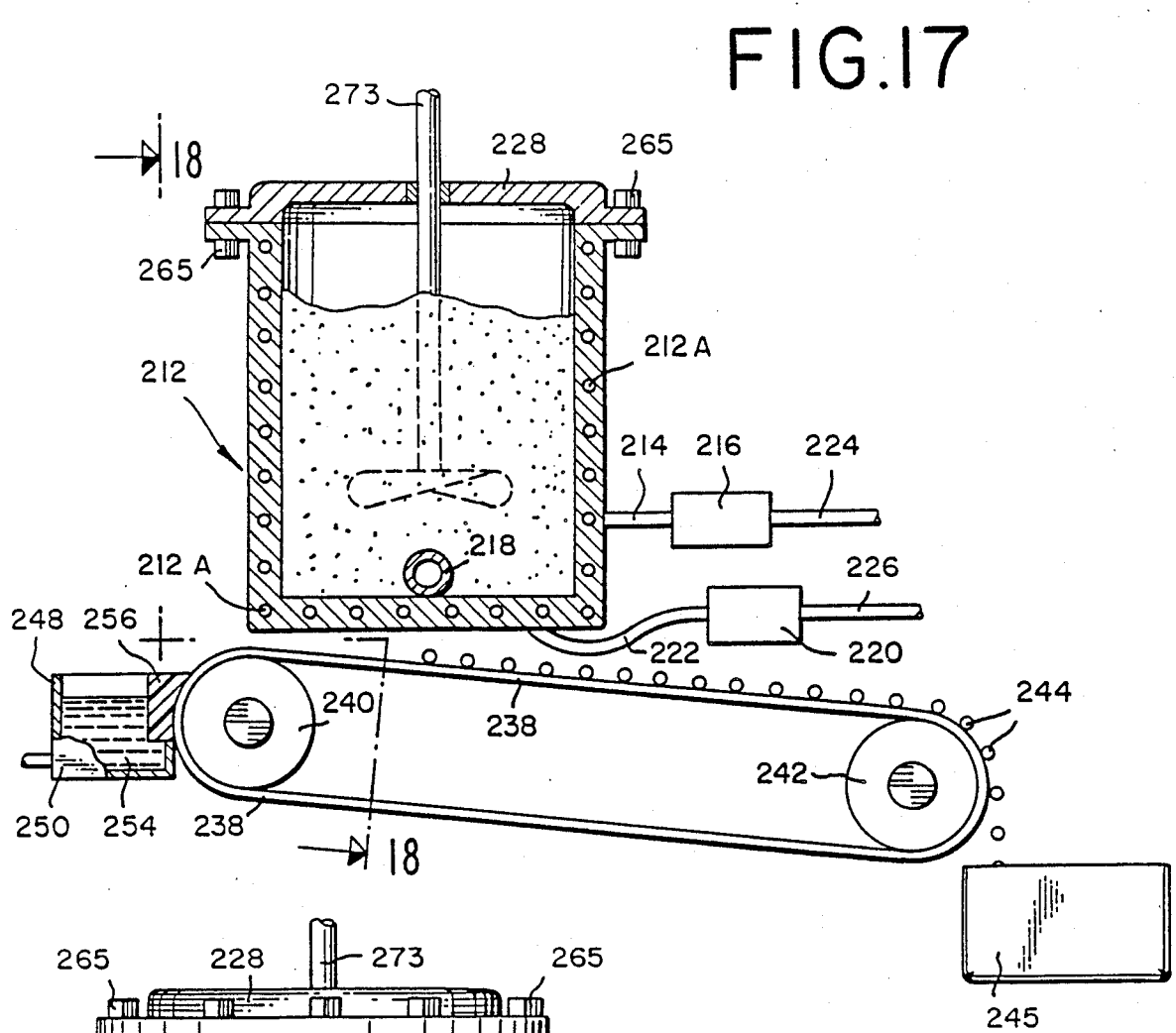

FIG. 17 represents a cut-away side elevation view of apparatus used in forming perfume polymers which contains embedded therein at least one of the adamantane derivatives of our invention.

Figure 18:
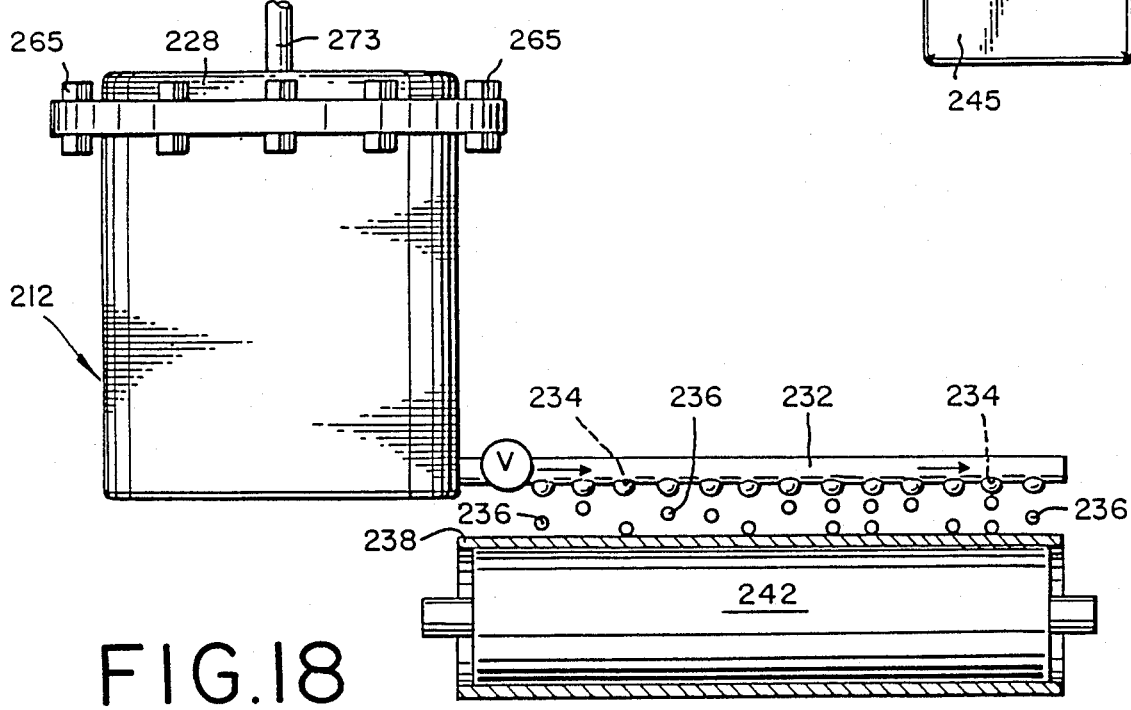

FIG. 18 is a front view of the apparatus of FIG. 17 looking in the direction of the arrows.

DETAILED DESCRIPTION OF THE DRAWINGS

Figure 1:
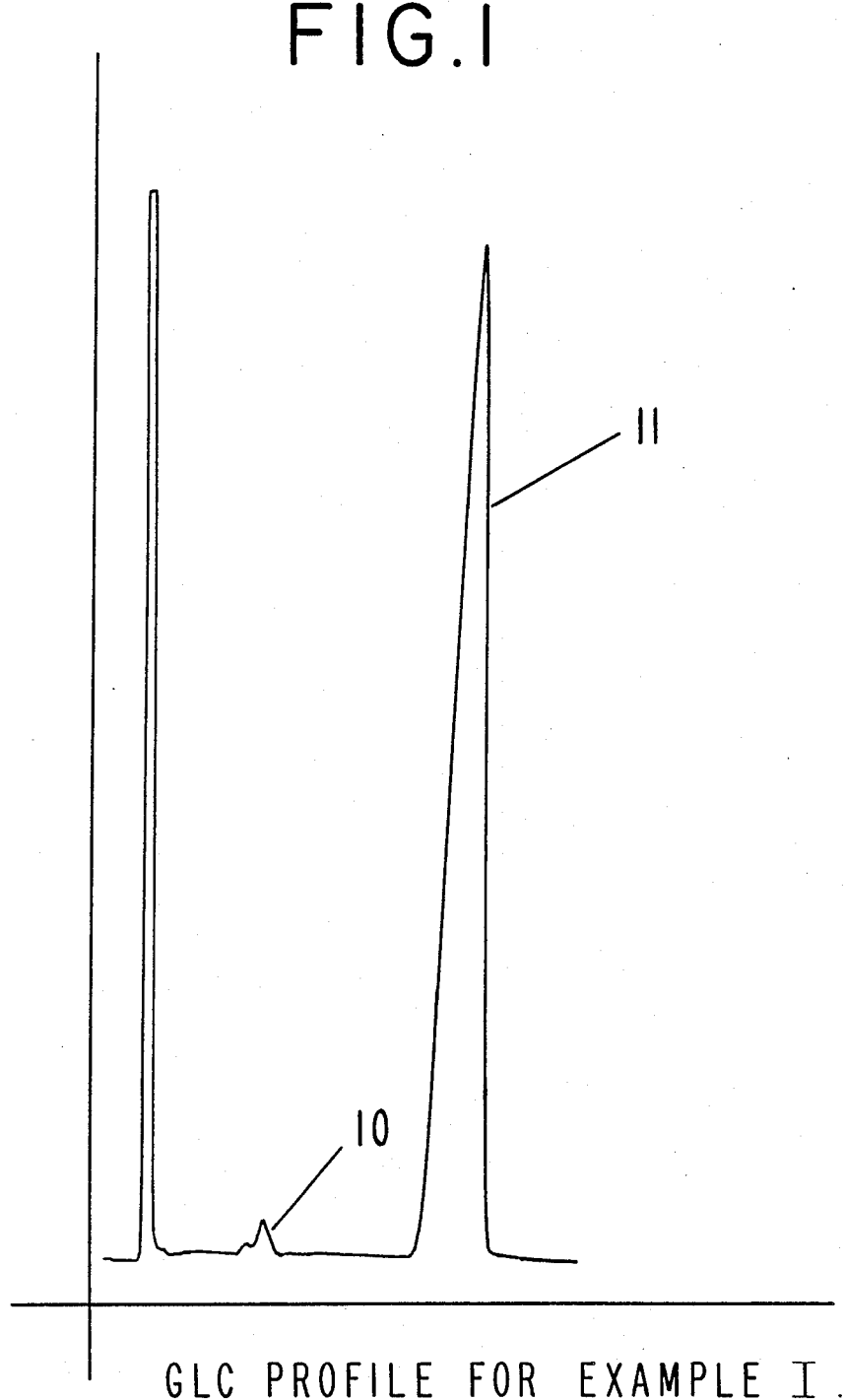
FIG. 1 is the GLC profile for the crude reaction product of Example I containing the compounds having the structures.

FIG. 1 is the GLC profile for the reaction product of Example I. The peak indicated by reference numeral 10 is the peak for the compound having the structure:

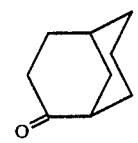

The peak indicated by reference numeral 11 is the peak for the compound having the structure:

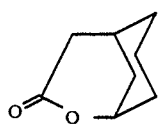

FIG. 3 is the GLC profile for the reaction product of Example II (Conditions: Carbowax column programmed at 150°–220° C. at 8° C.).

The peak indicated by reference numeral 20 is the peak for the compound having the structure:

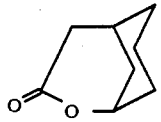

The peak indicated by reference numeral 21 is the peak for the compound having the structure:

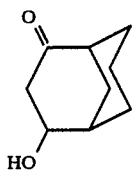

FIG. 5 is the GLC profile for the reaction product of Example III (Conditions: SE-30 column programmed at 150°–220° C. at 8° C. per minute).

The peaks indicated by reference numerals 50 and 51 are for isomers of the compound having the structure:

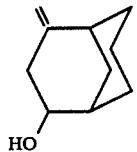

FIG. 7 is the GLC profile for the reaction product of Example IV. The peaks indicated by reference numeral 72 and 73 are for isomers of the compound defined according to the structure:

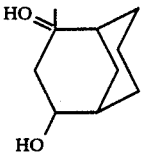

The peak indicated by reference numeral 71 is the peak for the compound having the structure:

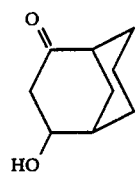

The peak indicated by reference numeral 70 is the peak for the compound having the structure:

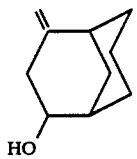

which compound is apparently formed during the trapping in the GLC column (Conditions: Carbowax column programmed at 150°–220° C. at 8° C. per minute).

FIG. 14 is the GLC profile for the reaction product of Example VI (Conditions: Carbowax column programmed at 100°–220° C. at 8° C. per minute). The peak indicated by reference numeral 140 is the peak for the compound having the structure:

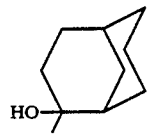

Referring to FIGS. 17 and 18 there is provided a process for forming scented polymer elements (wherein the polymer may be a thermoplastic polymer such as low density polyethylene or polypropylene or copolymers of ethylene and vinly acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 17 and 18, in particular, the apparatus used in producing such elements comprises a device for forming the polymer containing perfume, e.g., polyethylene or polyethylene-polyvinyl acetate or mixtures of the same of polypropylene, which comprises a vat or container 212 into which the polymer taken alone or in admixture with other copolymers and the perfuming substance which is at least one of the adamantane derivatives of our invention or mixtures of adamantane derivatives and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostate or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains one or more of the adamantane derivatives of our invention is quickly added to the melt. Generally, about 10-45 percent by weight of the resulting mixture of the perfumery substance is added to the polymer.

After the perfume material is added to the container 212, the mixture is stirred for a minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicty of orifices 234 adjacent to the lower side thereof. The outer end of the conduit 232 is closed so that the liquid polymer in intimate admixture with one or more of the adamantane derivatives of our invention or mixture of adamantane derivatives and one or more other substances, will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the adamantane derivatives of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instananeously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides adamantane derivatives defined according to the structure:

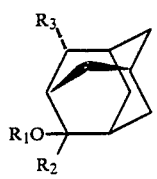

wherein $R_1$ is hydrogen or acetyl; $R_2$ is hydrogen or methyl; and $R_3$ is hydrogen or methylene; and the dashed line represents a carbon-hydrogen single bond or a carbon-methylene double bond with the provisos that when $R_2$ is methyl then $R_1$ and $R_3$ are both hydrogen; and when $R_2$ is hydrogen, $R_3$ is methylene and the dashed line represents a carbon-methylene double bond.

The adamantane derivatives of our invention produced according to prior art processes are known in the prior art per se and have now been found to be capable of augmenting or enhancing woody, earthy, camphoraceous, phenolic, piney, balsamic and patchouli-like aromas with camphoraceous, armoise, animalic, woody and minty topnotes thus fulfilling a need in the field of perfumery.

The processes for producing the adamantane derivatives of our invention are also known in the prior art and involve the following reactions which are also exemplified in Examples I-VI, infra:

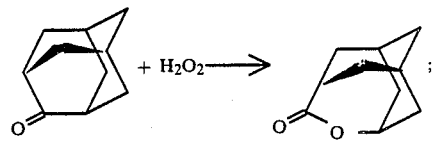

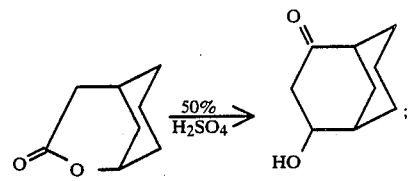

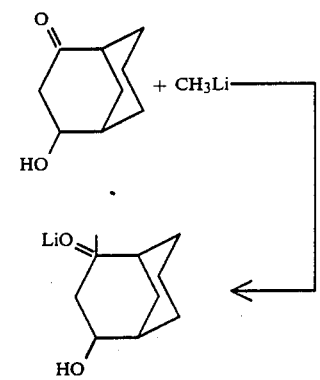

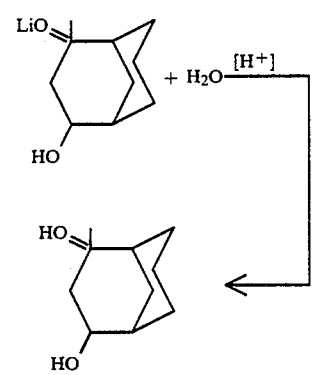

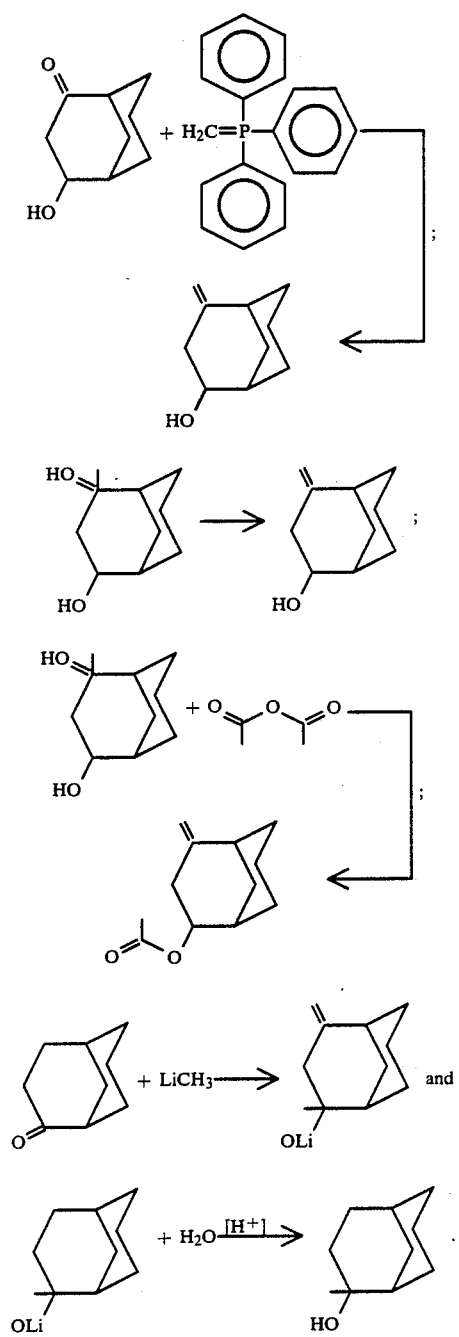

The following table represents the compounds the perfumery uses of which are the subject of our invention and their respective organoleptic properties:

TABLE I

| Structure of Compound | Perfumery Properties |
| --- | --- |
| The compound having the structure:<br>produced according to | An earthy, camphoraceous and phenolic aroma. |

TABLE I-continued

| Structure of Compound | Perfumery Properties |
| --- | --- |
| Example III. | |
| The compound having the structure:<br>produced according to Example V. | A piney, camphoraceous, balsamic and woody aroma with camphoraceous armoise and animalic topnotes. |
| The compound having the structure:<br>produced according to Example VI. | A camphoraceous, woody, patchouli aroma with camphoraceous, woody, minty and animalic topnotes. |

One of the adamantane derivatives prepared in accordance with the processes of the prior art and one or more auxilliary perfume ingredients including, for example, alcohols other than the hydroxy adamantane derivatives or our invention, aldehydes, ketones, terpenic hydrocarbons, nitriles, esters, other than the adamantane esters of our invention, lactones, natural essential oils and synthetic essential oils may be admixed so that the combined odors of the individual components produce a pleasant and desired fragrance, particularly, and preferably, in piney fragrances and patchouli fragrances. Such perfume compositions usually contain (a) the main note or the "bouquet" or foundation stone of the composition; (b) modifiers which round out an accompany the main note; (c) fixatives which include odorous substances which lend a particular note to the perfume throughout all states of evaporation and substances which retard evaporation; and (d) topnotes which are usually low-boiling fresh-smelling materials.

In perfume compositions, it is the individual components which contribute to their particular olfactory characteristics, however, the overall sensory effect of the perfume composition will be at least the sum total of the effects of each of the ingredients. Thus, one of the adamantane derivatives prepared in accordance with the processes or our invention can be used to alter, modify or enhance the aroma characteristics of a perfume composition, for example, by utilizing or moderating the olfactory reaction contributed by another ingredient in the composition.

The amount of one of the adamantane derivatives prepared in accordance with the processes of our invention which will be effective in perfume compositions as well as in perfumed articles (e.g., anionic, nonionic, cationic, or zwitterionic detergents, soaps and fabric softener compositions and articles) and colognes depends upon many factors including the other ingredients, their amounts and the effects which are desired. It has been found that perfume compositions containing as little as 0.01% of one of the adamantane derivatives prepared in accordance with the processes of our invention and less 50% of one of the adamantane derivatives prepared in accordance with the processes of our invention or even less (e.g., 0.005%) can be used to impart a woody, earthy, camphoraceous, phenolic, piney, balmsamic and patchouli aroma with camphoraceous, armoise, animalic, woody and minty topnotes to soaps, cosmetics, anionic, cationic, nonionic, or zwitterionic detergents, fabric softener compositions, fabric softener articles, perfumed polymers or other articles. The amount employed can range up to 70% of the fragrance components and will depend on considerations of cost, nature of the end product, the effect desired on the finished product and the particular fragrance sought.

One or more of the adamantane derivatives prepared in accordance with the prior art are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, perfumed polymers and the like. When used as (an) olfactory component(s) as little as 0.2% of one or both of the adamantane derivatives of our invention, prepared in accordance with the prior art of our invention, will suffice to impart an intense and substantive woody, earthy, camphoraceous, phenolic, piney, balsamic and patchouli aroma with camphoraceous, armoise, animalic, woody and minty topnotes to patchouli formulations and to vetiver formulations and to pine formulations. Generally, no more than 6% of one or both of the adamantane derivatives of our invention produced in accordance with the processes of our invention based on the ultimate end product are required in the perfumed article composition. Accordingly, the range of one or more of the adamantane derivatives of our invention in a perfumed article may vary from one 0.2% up to about 6% by weight of the ultimate perfumed article.

In addition, the perfumed compositions or fragrance compositions of our invention can contain a vehicle or carrier for one or both of the adamantane derivatives prepared in accordance with the processes of our invention. The vehicle can be a liquid, such as a non-toxic alcohol, e.g., ethyl alcohol, a glycol, e.g., propylene glycol or the like. The carrier can also be an absorbent solid, such as a gum (i.e., gum arabic, xanthan or guar gum) or components for encapsulating the composition (such as gelatin as by coacervation or such as a urea-formaldehyde pre-polymer when forming a urea-formaldehyde polymer wall around a liquid perfume center.

It will thus be apparent that one of the adamantane derivatives of our invention can be utilized either to alter, modify or enhance sensory properties, particularly organoleptic properties such as fragrances of a wide variety of consumable materials.

The following examples illustrate methods (primarily disclosed in the prior art) used to manufacture the adamantane derivatives useful in our invention.

Examples following Example VI (Example VII et seq) illustrate the organoleptic utilities of the adamantane derivatives of our invention.

All parts and percentages given herein are by weight unless otherwise specified.

EXAMPLE I

Preparation of 4-Oxahomoadamantan-5-One

Reaction:

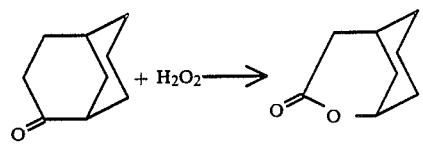

Into a three liter reaction-flask equipped with stirrer, thermometer, reflux condenser and heating mantle is placed 13.32 grams of sclenium dioxide and 1251 ml pre-warmed tertiary buytl alcohol. While maintaining the temperature at 22°-26° C. over a period of 15 minutes, 225 grams (2.06 moles) of hydrogen peroxide (30%) is added to the reaction mass.

The reaction mass is then heated to reflux (76° C.). While maintaining the reaction temperature at 76°-78° C., over a period of 0.5 hours, 300 grams (2.01 moles) of the compound having the structure

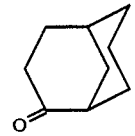

(adamantanone) is added to the reaction mass.

The reaction mass is then refluxed for a period of 1.5 hours after which time an additional 34 grams (0.3 moles) of 30% hydrogen peroxide is added drop-wise to the reaction mass.

The reaction mass is allowed to cool down to room temperature for a period of 12 hours.

The reaction mass is then poured into 1,500 ml cold water. The reaction mass is then extracted with three 1,500 ml portions of methylene dichloride. The organic layer is washed with 2,000 ml water and then dried over anhydrous magnesium sulfate. The resultant slurry is filtered and concentrated to yield 326 grams of crude product. The crude product is dissolved in 100 ml methylene dichloride and then diluted with n-hexane to yield 1,100 ml product.

The reaction mass is then concentrated for further reaction.

EXAMPLE II

Preparation of 4-Hydroxytricyclo [3.3.1.1] Decan-2-One

Reaction:

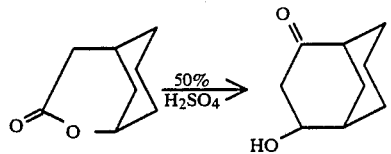

Into a 2 liter reaction flask equipped with ice bath is placed 500 ml concentrated sulfuric acid. While maintaining the concentrated sulfuric acid at 24° C., over a period of 0.3 hours 500 ml water is added. The reaction mass is then cooled to 30° C. and while maintaining the reaction mass at 30°-31° C., 96 grams (0.58 moles) of the compound having the structure:

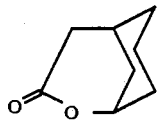

added to the reaction mass.

The reaction mass is then heated to 90° C. and maintained at 90° C. initially for a period of 1 hour. The reaction mass is then aged for 2.5 hours yielding 52% compound having the structure:

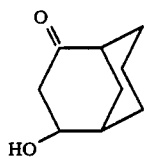

and 45% of the compound having the structure:

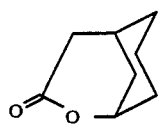

(the starting material). After 3½ hours of aging the reaction mass contains 61% of the compound having the structure:

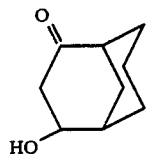

and 36% of the compound having the structure:

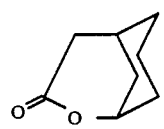

After 5 hours of aging the reaction mass contains 65% of the compound having the structure:

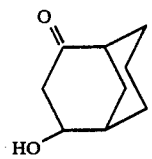

and 35% of the compound having the structure:

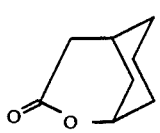

250 ml concentrated sulfuric acid is then to the reaction mass. The reaction mass is then aged at 90° C. for 7.5 hours.

The reaction mass is then poured into one liter of water and the products are extracted with three 1,000 ml portions of methylene dichloride. The organic layer is washed with water (1,000 ml) and dried over anhydrous magnesium sulfate, filtered and concentrated to yield 63 grams of product containing 78% of the compound having the structure:

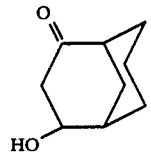

EXAMPLE III

Production of Methylene Hydroxyadamantane Derivative Using Witting Reaction

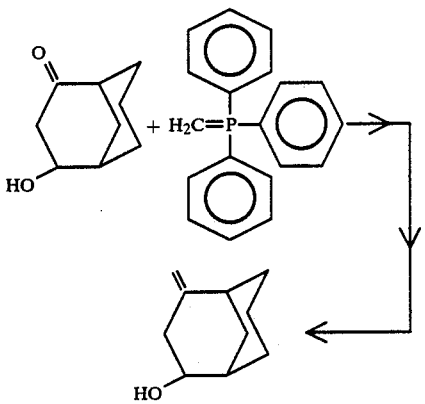

Into a 250 ml reaction flask equipped with thermometer, addition funnel and dry ice/isopropyl alcohol bath is placed a slurry of trimethyl phosphine bromide (26.8 grams; 0.075 moles) in 75 ml tetrahydrofuran. With vigorous stirring, the resulting slurry is cooled to 0° C.

Dropwise while maintaining the temperature at 0° C., 52 ml of a 1.6 molar solution of n-butyl lithium in hexane is added to the flask. (Addition time:20 minutes).

The resulting slurry is aged at 15 minutes with stirring at 0° C.

Over a period of 20 minutes while maintaining the reaction temperature at 0° C., 5 grams (0.03 moles; of the compound having the structure:

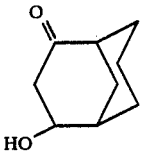

prepared according to Example II (in diglyme solvent) is added to the reaction mass. The reaction mass is then aged for 2 hours while being permitted to warm to room temperature.

The resulting suspension is filtered and the solid is washed with 30 ml methylene dichloride.

The organic layer is then washed with 250 ml saturated sodium chloride. The water layer is extracted with 50 ml methylene dichloride.

All organic layers are combined and dried over anhydrous magnesium sulfate. The filtrate is then concentrated to yield 12 grams of material.

The resulting concentrate is chromatographed to yield in three fractions; weighing:

(i) 130 mg;
(ii) 450 mg; and
(iii) 30 mg 450 mg fraction is the compound having the structure:

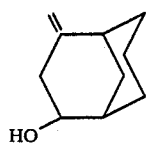

EXAMPLE IV

Preparation of Tertiary Methyl Adamantane Diol Followed by Creation of Methylene Adamantol Reactions:

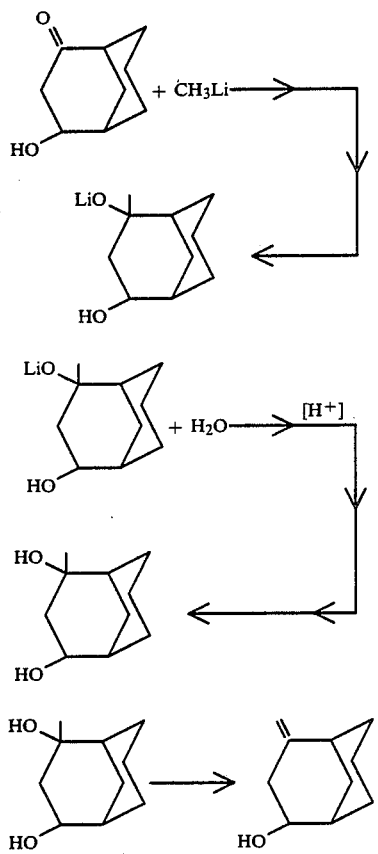

Into a 250 ml reaction flask equipped with a dry ice/isopropyl alcohol bath is placed 54 ml of a 1.4 molar solution of methyl lithium is diethyl ether (0.075 moles). the methyl lithium solution is cooled to −5° C. and over a period of 0.5 hours, 5 grams (0.03 moles) of the compound having the structure:

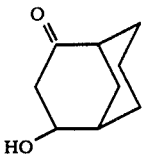

prepared according to Example II in methylene dichloride is added to the methyl lithium solution. The reaction mass is then cooled to −10° C. The reaction mass is then allowed to warm to room temperature and aged at room temperature for 5 hours.

50 ml water is added to the reaction mass. The resulting organic phase is then washed with three 250 ml portions of saturated sodium chloride until neutral to pH paper.

The organic layer is dried over anhydrous magnesium sulfate, filtered and concentrated to yield 2.5 grams (0.014 moles) of product having the structure:

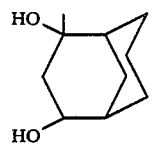

The resulting product is then dehydrated over methane sulfonic acid to yield the compound having the structure:

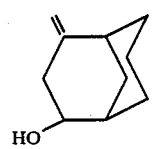

EXAMPLE V

Preparation of 4-Hydroxy Tricyclo [3.3.1.1] 2-Methylene Decane Acetate

Reaction:

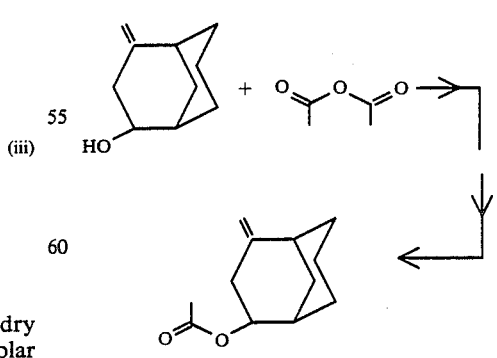

Into a 50 ml reaction flask equipped with magnetic stirrer is placed 5 grams (0.03 moles) of the compound having the structure:

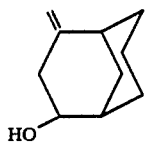

dissolved in 25 ml acidic anhydride.

The resulting mixture is heated to 90° C. and maintained with stirring at 90° C. for a period of 2 hours.

At the end of the 2 hour period 10 ml water is slowly added while maintaining the reaction temperature at 90° C. with stirring.

The reaction mass is heated to 105° C. briefly.

The reaction mass is then poured into 100 ml water.

The reaction mass is extracted with three 40 ml portions of methylene dichloride.

The organic phase is washed with two 100 ml portions of saturated sodium bicarbonate followed by one 100 ml portion of sodium chloride (saturated).

The reaction mass is then filtered through anhydrous magnesium sulfate and concentrated.

The resulting oily solid is washed n-hexene. The resulting product is filtered and the filtrate is concentrated to yield 6 grams (0.02 moles). The resulting product is distilled at 95° C. and 2 mm Hg, yielding 3.25 grams (0.0158 moles) of product having the structure:

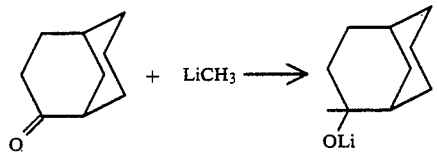

EXAMPLE VI

Preparation of Tertiary Methyl Adamantol

Reactions

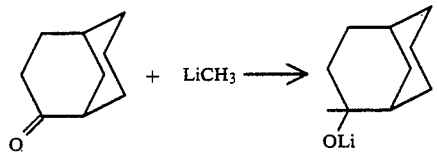

(i)

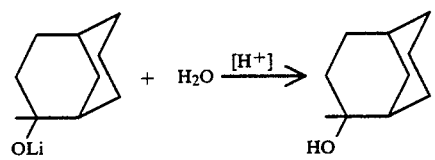

(ii)

Into a 5 liter flask equipped with cooling bath, stirrer, thermometer and reflux condenser and under a nitrogen blanket is added 2.80 moles of methyl lithium dissolved in 800 cc diethyl ether. While maintaining the reaction mass at −2° C. over a period of 1 hour, 205 grams of 2-adamantanone having the structure:

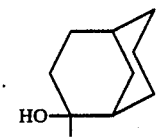

is added to the reaction mass. The resulting product is maintained at 4° C. for a period of one hour.

Dropwise over a period of 1 hour 700 cc of 5% acidic acid is added to the reaction mass. Dropwise over a period of 1 hour 700 cc of toluene is added to the reaction mass with stirring.

The reaction mass is then washed with 800 cc of 5% acidic acid followed by two portions (800 cc each) of 5% sodium bicarbonate followed by two 800 cc portions of sodium chloride (saturated).

The resulting product is filtered and has the structure:

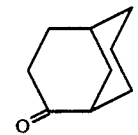

EXAMPLE VII

Pine Fragrance

The following pine fragrance formulation is produced:

TABLE I

| Ingredients | VII(A) | VII(B) | VII(C) |
|---|---|---|---|
| Isbornyl acetate | 100 | 100 | 100 |
| Camphor | 10 | 10 | 10 |
| Terpineol | 25 | 25 | 25 |
| Fir balsam absolute (50% in diethyl phthalate) | 20 | 20 | 20 |
| Courmarin | 4 | 4 | 4 |
| Linalool | 30 | 30 | 30 |
| Fenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-trimethyl-1-cyclohexene-1-caboxaldehyde | 12 | 12 | 12 |
| Maltol (1% in diethyl phthalate) | 5 | 5 | 5 |
| The compound having the structure: 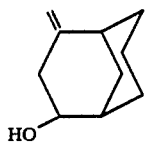 prepared according Example III. | 28 | 0 | 0 |
| The compound having the structure: | 0 | 28 | 0 |

TABLE I-continued

| Ingredients | VII(A) | VII(B) | VII(C) |
|---|---|---|---|

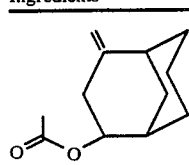

prepared according to
Example V.

The compound having      0    0    28
the structure:

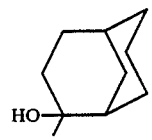

prepared according
Example VI.

The compound having the structure:

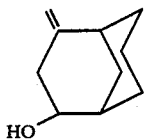

prepared according to Example III adds an earthy, camphoraceous and phenolic undertone to this pine fragrance. Accordingly, the fragrance of Example VII(A) can be described as "piney with earthy, camphoraceous and phenolic undertones".

The compounds having the structure:

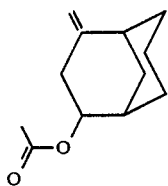

prepared according to Example V adds to this piney fragrance a camphoraceous, balsamic and woody undertone with camphoraceous, armoise and animalic topnotes. Accordingly, the fragrance of Example VII(B) can be described as "piney with camphoraceous, balsamic and woody undertones and camphoraceous, armoise and animalic topnotes".

The compound having the structure:

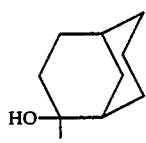

adds to this piney fragrance a camphoraceous, woody and pathcouli undertone and camphoraceous, animalic, woody and minty topnotes. Accordingly, the fragrance of Example VII(C) can be described as "piney with camphoraceous, woody and patchouli undertones and camphoraceous, animalic, woody and minty topnotes.

EXAMPLE VIII

Preparation of Cosmetic Powder Compositions

Cosmetic powder compositions are prepared by mixing in ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| The compound having the structure: 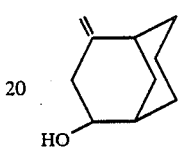 prepared according to Example III. | An earthy, camphoraceous and phenolic aroma profile. |
| The compound having the structure: 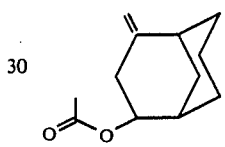 prepared according to Example V. | a piney, camphoraceous, balsamic and woody aroma profile with camphoraceous armoise, and animalic topnotes. |
| The compound having the structure: 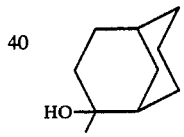 prepared according to Example VI. | A camphoraceous, woody, and patchouli aroma with camphoraceous, animalic, woody and minty topnotes. |
| The perfume composition of Example VII(A) | Piney with earthy, camphoraceous and phenolic undertones. |
| The perfume composition of Example VII(B) | Piney with camphoraceous, balsamic and woody undertones and camphoraceous, armoise and animalic topnotes. |
| The perfume composition of Example VII(C) | Piney with camphoraceous, woody and patchouli undertones and camphoraceous, animalic, woody and minty topnotes. |

EXAMPLE IX

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example VIII are prepared containing 0.10%, 0.15%, 0.20%, 0.25%, 0.30% and 0.35% of the substance set forth in Table II of Example VIII. They are prepared by adding and homogeneously mixing the appropriate quantity of substance set forth in Table II of Example VIII below in the liquid detergent. The detergents all possess excellent aromas as set forth in Table III of Example VIII, the intensity increasing with greater concentrations of substance as set forth in Table II of Example VIII.

EXAMPLE X

Preparation of Colognes and Handerchief Perfumes

Compositions as set forth in Table II of Example VIII are incorporated into colognes at concentrations of 2.0%, 2.5%, 3.0%, 3.5%, 4.0%, 4.5% and 5.0% in 80%, 85%, 90% and 95% aqueous food grade ethanol solutions, and into handkerchief perfumes at concentrations of 15%, 20%, 25% and 30% (in 80%, 85%, 90% and 95% aqueous food grade ethanol solutions). Distinctive and definitive fragrances as set forth in Table II of Example VIII are imparted to the colognes and to the handkerchief perfumes at all levels indicated.

EXAMPLE XI

Preparation of Soap Compositions

One hundred grams of soap chips [per sample] (IVORY ®, produced by the Procter & Gamble Company of Cincinnati, Ohio), are each mixed with one gram samples of substances as set forth in Table III of Example VIII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VIII.

EXAMPLE XII

Preparation of Solid Detergent Composition

Detergents are prepared using the following ingredients according to Example I of Canadian Pat. No. 1.007,948:

| Ingredient | Percent By Weight |
|---|---|
| "Neodol ® 45-11(a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VIII. Each of the detergent samples has an excellent aroma as indicated in Table II of Example VIII.

EXAMPLE XIII

Utilizing the procedure of Example I at column 15 of U.S. Pat. No. 3,632,396, non-woven cloth substrates useful as dryer added fabric softening articles of manufacture are prepared wherein the substrate, the substrate coating and the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.);
   57%—$C_{20-22}$HAPS
   22%—isopropyl alcohol
   20%—antistatic agent
   1%—of one of the substances as set forth in Table II of Example VIII.

Fabric softening compositions prepared according to Example I at column 15 of U.S. Pat. No. 3,632,396 having aroma characteristics as set forth in Table II of Example VIII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example VIII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softner non-woven fabrics and these aroma characteristics are described in Table II of Example VIII.

EXAMPLE XIV

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following are added to the PVP/VA alcoholic solution:

| Ingredient | Percent By Weight |
|---|---|
| Dioctyl sebacate | 0.05 |
| Benzyl alcohol | 0.10 |
| Dow Corning 473 fluid (prepared by the Dow Corning Corporation) | |
| Tween 20 surfactant (prepared by ICI America Corporation) | 0.03 |
| One of the perfumery substances as set forth in Table II of Example VIII | 0.10 |

The perfuming substances as set forth in Table II of Example VIII add aroma characteristics as set forth in Table II of Example VIII which are rather intense and aesthetically pleasing to the users of the soft-feed, good-hold pump hair sprays.

EXAMPLE XV

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

Gafquat®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 disterate produced by Armak Corporation.

The resulting material is then mixed and cooled to 45° C. and 0.3 weight percent of perfuming substance as set forth in Table II of Example VIII is added to the mixture. The resulting mixture is cooled to 40° C. and blending is carried out for an additional one hour in each case. At the end of this blending period, the resulting material has a pleasant fragrance as indicated in Table II of Example VIII.

What is claimed is:

1. A process for augmenting or enhancing the aroma of a perfume composition cologne or perfumed article comprising the steps of adding to said perfume composition, cologne or perfumed article an aroma augmenting or enhancing amount of the adamantane derivatives having the structure:

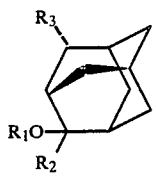

wherein $R_1$ is hydrogen or acetyl; $R_2$ is hydrogen or methyl; $R_3$ is hydrogen or methylene; and the dashed line is a carbon hydrogen single bond or a carbon-methylene double bond with the provisos that when $R_2$ is methyl, $R_1$ and $R_3$ are hydrogen and when $R_2$ is hydrogen, $R_3$ is methylene and the dashed line is a carbon-methylene double bond.

2. The process of claim 1 wherein the adamantane derivative has the structure:

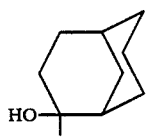

3. The process of claim 1 wherein the adamantane derivative has the structure:

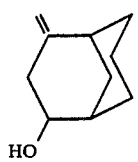

4. The process of claim 1 wherein the adamantane derivative has the structure:

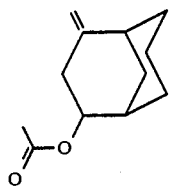

5. A perfume composition comprising a perfume base and intimately admixed therewith an aroma augmenting or enhancing quantity of at least one compound defined according to the structure:

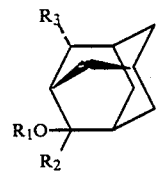

wherein $R_1$ is hydrogen or acetyl; $R_2$ is hydrogen or methyl; $R_3$ hydrogen or methylene; and the dashed line is a carbon hydrogen single bond or a carbon-methylene double bond with the provisos that when $R_2$ is methyl, $R_1$ and $R_3$ are hydrogen and when $R_2$ is hydrogen, $R_3$ is methylene and the dashed line is a carbon-methylene double bond.

6. A perfumed article comprising a perfumed article base and intimately admixed therewith an aroma augmenting or enhancing quantity of at least one adamantane derivative defined according to the structure:

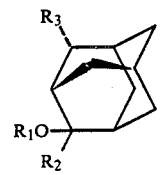

wherein $R_1$ is hydrogen or acetyl; $R_2$ is hydrogen or methyl; $R_3$ hydrogen or methylene; and the dashed line is a carbon hydrogen single bond or a carbon-methylene double bond with the provisos that when $R_2$ is methyl, $R_1$ and $R_3$ are hydrogen and when $R_2$ is hydrogen, $R_3$ is methylene and the dashed line is a carbon-methylene double bond.

7. A perfumed polymer comprising a microporous polymer matrix and intimately admixed therewith an aroma augmenting or enhancing quantity of at least one adamantane derivative defined according to the structure:

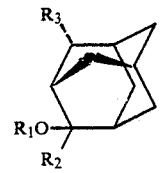

wherein $R_1$ is hydrogen or acetyl; $R_2$ is hydrogen or methyl; $R_3$ hydrogen or methylene; and the dashed line is a carbon hydrogen single bond or a carbon-methylene double bond with the provisos that when $R_2$ is methyl, $R_1$ and $R_3$ are hydrogen and when $R_2$ is hydrogen, $R_3$ is methylene and the dashed line is a carbon-methylene double bond.

* * * * *